United States Patent
Haas et al.

(10) Patent No.: US 7,096,091 B2
(45) Date of Patent: Aug. 22, 2006

(54) MODULAR ROBOTIC SYSTEM AND METHOD FOR SAMPLE PROCESSING

(75) Inventors: Hansjoerg Werner Haas, Burlington (CA); Trevor Gordon Jones, Ancaster (CA); Roger Barry Hertz, Burlington (CA); Daniel Curtis McCrackin, Hamilton (CA); Edgar Alllison Outhouse, Toronto (CA); Thomas Ian Hatherley, Oakville (CA); Michael Paul Riff, Burlington (CA); Gregory Earl Lowe, Mississauga (CA); Richard Alexander Huber, St. Catherines (CA); Jonathan David Wittchen, Burlington (CA); Bradley Kenneth Klink, Burlington (CA)

(73) Assignee: Thermo CRS Ltd., Burlington (CA)

( * ) Notice: Subject to any disclaimer, the term of this patent is extended or adjusted under 35 U.S.C. 154(b) by 101 days.

(21) Appl. No.: 10/898,180

(22) Filed: Jul. 26, 2004

(65) Prior Publication Data

US 2005/0075757 A1 Apr. 7, 2005

Related U.S. Application Data

(63) Continuation of application No. PCT/CA03/00106, filed on Jan. 27, 2003
(60) Provisional application No. 60/350,943, filed on Jan. 25, 2002.

(51) Int. Cl.
*G06F 19/00* (2006.01)

(52) U.S. Cl. .................. 700/245; 700/250; 700/254; 700/262; 901/1; 414/799

(58) Field of Classification Search .............. 700/245, 700/250, 254, 262; 414/799, 801, 806; 901/7, 901/8, 30, 31; 198/418.2, 465.2; 483/1, 14, 483/901
See application file for complete search history.

(56) References Cited

U.S. PATENT DOCUMENTS

| 4,679,297 | A | * | 7/1987 | Hansen, Jr. et al. ............. 483/1 |
| 4,773,523 | A | * | 9/1988 | Hansen, Jr. et al. ......... 414/799 |
| 6,881,579 | B1 | * | 4/2005 | Hilson et al. .................. 436/47 |
| 2003/0032191 | A1 | * | 2/2003 | Hilson et al. .................. 436/47 |
| 2004/0106145 | A1 | * | 6/2004 | Gold et al. ..................... 435/6 |

FOREIGN PATENT DOCUMENTS

| JP | 2001-174468 | 6/2001 |
| WO | WO 96/25712 A1 | 8/1996 |
| WO | WO 00/60361 A2 | 10/2000 |

OTHER PUBLICATIONS

Payandeh et al., A control architecture for arm/hand manipulating system, 1991, IEEE, p. 1440–1443.*

* cited by examiner

Primary Examiner—Thomas G. Black
Assistant Examiner—McDieunel Marc
(74) Attorney, Agent, or Firm—John R. S. Orange; Santosh K. Chari; Blake, Cassels & Graydon LLP

(57) ABSTRACT

A method of processing objects using a bilateral architecture. The method comprises the steps of: arranging a plurality of instruments around a bi-directional conveyance device, the instruments spaced at fixed pitch intervals along the conveyor device; assigning dedicated movers to each of the instruments, the dedicated movers for loading and unloading of the objects to and from the instruments and the conveyance device; and controlling the operation of the conveyance device to have an interrupted motion, the interrupted motion for co-ordinating the loading and unloading of the objects; wherein the dedicated movers are positioned such that adjacent movers operate independently of one another. The method can be operated on an automated robotic system having a modular architecture. The system comprises; a backbone having a plurality of backbone connectors; a module having a module connector for releasably coupling with a respective one of the backbone connectors; a bi-directional motion device connected to the backbone, the motion device for presenting an object adjacent to the module when the module is coupled to the backbone; a connection interface formable by coupling the backbone and module connectors, the connection interface for providing an operation coupling between the backbone and the module when adjacent thereto; wherein the connection interface provides a repeatable connection and disconnection capability between the backbone and the module for ready reconfiguration of the modular architecture.

51 Claims, 16 Drawing Sheets

MODULAR ROBOTIC SYSTEM AND METHOD FOR SAMPLE PROCESSING

This application claims priority from U.S. provisional application No. 60/350,943 filed on Jan. 25, 2002 and is a continuation of international application PCT/CA03/00106 filed on Jan. 27, 2003.

BACKGROUND OF THE INVENTION

1. Field of Invention

The present invention relates to automated robotic systems, and in particular to adaptable processing of samples.

2. Description of the Prior Art

In recent years, researchers are beginning to use robotics and automation more frequently to address issues such as sample processing, throughput, and reliability of results. Automated sample handling is quickly becoming a necessity due to sterility requirements and desired cost reductions. Further motivation for automated handling is the introduction of new technologies, such as miniaturization, higher sample density storage, smaller sample volumes, and increased precision to name a few. It is common in industry to use robotic systems with a single robotic device to feed multiple workstations in an automated system. However, one disadvantage of these systems is that the sample throughput is rate-limited by the limited ability of the robot when required to feed multiple workstations.

Recently, a number of dedicated automation systems are addressing the throughput needs. However, these dedicated systems can be limited in their adaptability, for example, to new assay requirements. It is common in the research environment that assay requirements change constantly, thereby making dedicated automation systems become either obsolete after the end of a campaign, or require extensive retooling to adjust to the new assay needs.

A more recent approach of automated systems is to use sequential sample processing devices. These systems can often address the throughput requirement of an assay and have some flexibility to be adjusted to changing needs. Nevertheless, in a chemical assay some steps may be repeated several times, meaning that in a sequential approach such devices have to be present in multiples, resulting in inefficient use of the process devices and unnecessarily high capital investment costs.

For example, automated robotic systems may contain third party equipment, such pipettors, incubators, readers and other third party equipment, which may not be built for a 24 hour operation and therefore be prone to failure. In such a situation, it is critical that an instrument can be replaced quickly without major intervention of the run.

It is an object of the present invention to provide a robotic modular system and method to obviate or mitigate at least some of the above-presented disadvantages.

SUMMARY OF THE INVENTION

According to the present invention there is provided a method of processing objects using a bilateral architecture. The method comprises the steps of: arranging a plurality of instruments around a bi-directional conveyance device, the instruments spaced at fixed pitch intervals along the conveyance device; assigning dedicated movers to each of the instruments, the dedicated movers for loading and unloading of the objects to and from the instruments and the conveyance device; and controlling the operation of the conveyance device to have an interrupted motion, the interrupted motion for coordinating the loading and unloading of the objects; wherein the dedicated movers are positioned such that adjacent movers operate independently of one another.

According to a further aspect of the present invention there is provided an automated robotic system having a modular architecture. The system comprises: a backbone having a plurality of backbone connectors; a module having a module connector for releasably coupling with a respective one of the backbone connectors; a bi-directional motion device connected to the backbone, the motion device for presenting an object adjacent to the module when the module is coupled to the backbone; a connection interface formable by coupling the backbone and module connectors, the connection interface for providing an operational coupling between the backbone and the module when adjacent thereto; wherein the connection interface provides a repeatable connection and disconnection capability between the backbone and the module for ready reconfiguration of the modular architecture.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

Figure 1:
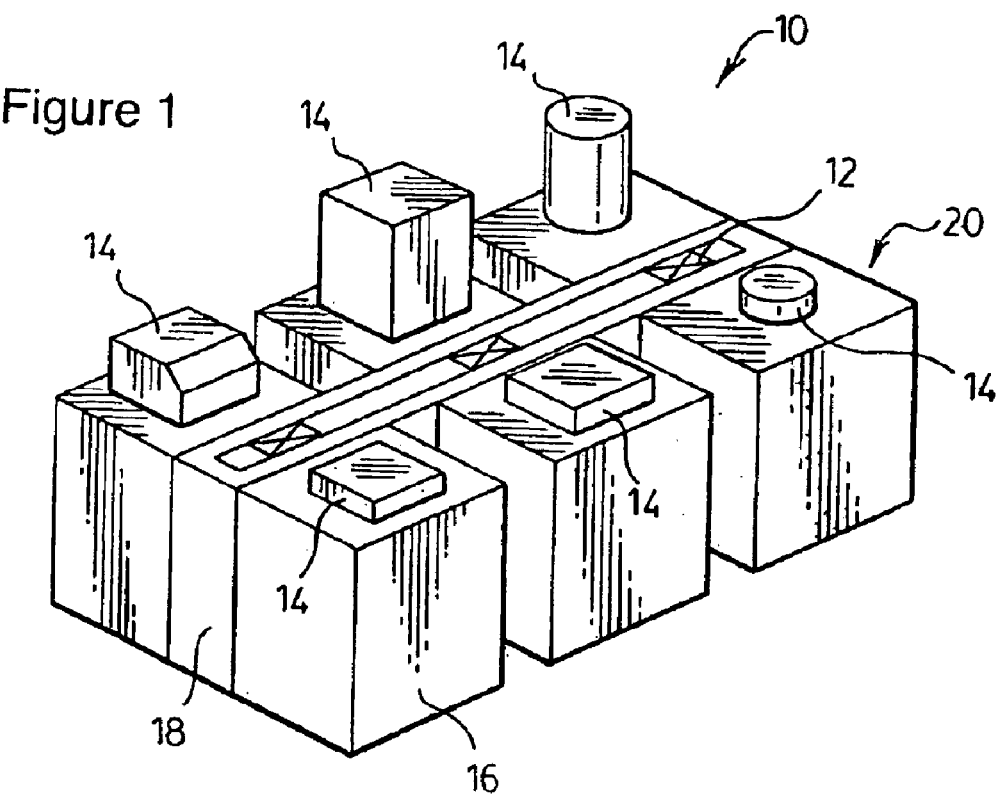
FIG. 1 shows a modular sample processing system.

Referring to FIG. 1, a robotic system 10 is shown for processing a variety of samples 12 in a random flow by different process instruments 14. The robotic system 10 encompasses a method for processing the samples 12 using labware such as microtiterplates, filterplates, pipette-tip boxes and the like (not shown). The robotic system 10 has a modular architecture, consisting of a central backbone 18 and an arrangement of detachable modules 16 coupled to the backbone 18. The modules 16 carry the process instruments 14 for effecting a specific operation on the samples 12, preferably in sequence. The process instruments 14 can be mounted on a tabletop 20 of the modules 16, underneath the table 20, or on levels above the tabletop 20 as further described below. The structure of the robotic system 10 facilitates the attachment of the modules 16 on both sides of the backbone 18, meaning that one-sided or double-sided robotic systems 10 can be built. Preferably, the modules 16 represent self-contained processing units with instruments 14, and are connectable to the central backbone 18 in a modular and interchangeable fashion.

Figure 2:
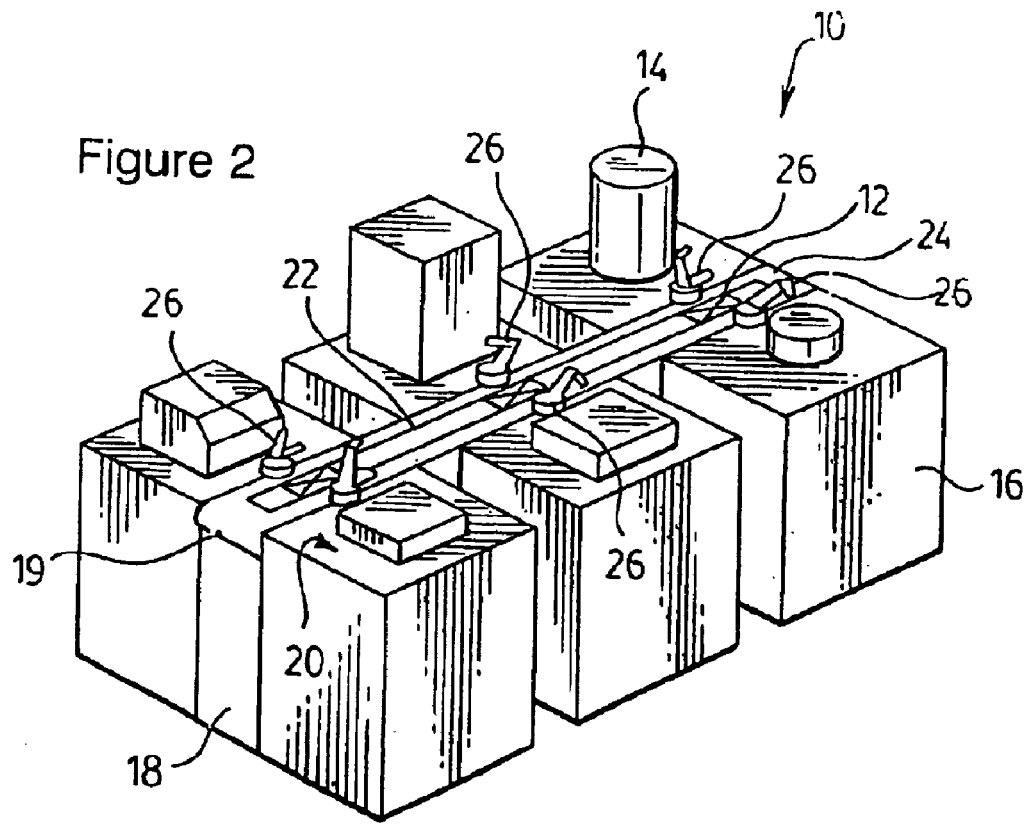
FIG. 2 shows the system of FIG. 1 with dedicated local movers.

Referring to FIG. 2, the backbone 18 includes a bi-directional high-speed distributed motion device 19, such as a conveyor, which serves as a central sample 12 mover. The design of the backbone 18 can be comprised of coupled modular conveyor components 22, 24, which provides for extension of the backbone 18 to accommodate different sized sample 12 processing sequences. Dedicated resources for loading and unloading (referred to as local movers 26) are mounted on the modules 16 or on the backbone 18 to serve each process instrument 14, or group of instruments 14 if desired. The design of the bi-directional high-speed motion device 19 allows multiple samples 12, such as but not limited to plates, to be moved to and from the coupled components 22, 24 simultaneously. The process modules 16 may be spaced at a fixed pitch along the motion device 19 to ease positioning of the process instruments 14 with respect to the samples 12. The local movers 26 can be situated on the modules 16 so as to address virtually any laboratory instrument 14 directly situated on the respective module 16. Multi-deck positions on the tables 20 can also be addressed using the local mover 26 mounted on a linear slide mechanism 28 (see FIG. 3), which changes the planar position of the local mover 26 on the table 20 with respect to the respective process instrument 14.

Referring again to FIG. 2, the method steps of processing samples 12 in the robotic system 10 can be separated into three separate phases: namely a) place the sample 12 on the conveyor 19, where the sample 12 is picked out of the instrument 14 by the respective local mover 26, moved, and placed on to the conveyor 19; b) convey the sample 12, where the conveyor 19 moves one or more of the contained samples 12 from one set of modules 16 to another set of modules 16; c) place the sample 12 in the instrument 14, where the sample 12 is picked off the conveyor 19 and placed into the instrument 14 by the dedicated local mover 26. The synchronization of the central movement action of the conveyor 19 with the local movers 26 provides for loading and unloading of the samples 12 in parallel, which helps to increase the overall loading/unloading efficiency of the robotic system 10. Accordingly, the overall sample 12 throughput of the robotic system 10 can be increased over other non-parallel systems by the provision of parallel operation, due to "distributed motion", between the central mover function of the conveyor 19 and the local movers 26 associated with dedicated process instruments 14.

Figure 3:
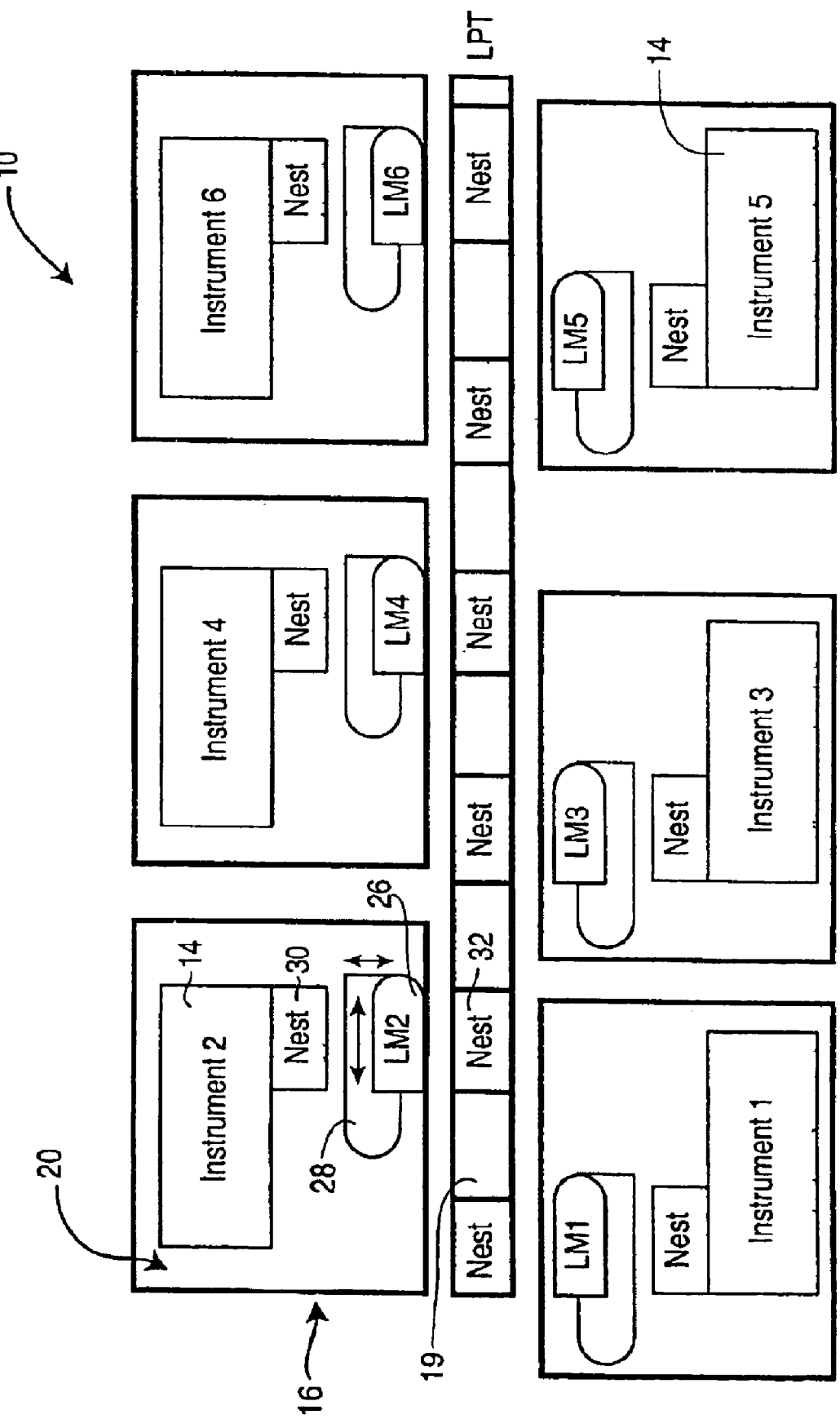
FIG. 3 shows a high speed distributed mover array of the system of FIG. 2.

Referring to FIG. 3, a material processing system embodiment of the robotic system 10 is shown. Objects or samples (not shown for clarity) are moved between the processing instruments 14. Each processing instrument 14 has the local object mover 26 which can pick up objects from respective access nests 30 of the processing instruments 14, and move the objects to the central conveyer 19 onto a respective central nest 32. The local movers 26 can also pick up objects from central nests 32 of the central conveyer 19 and place the objects into the access nests 30.

Referring again to FIG. 3, the central conveyer 19 is capable of bi-directional motion, and has one or more central access nests 32 into which the objects may be placed. The processing instruments 14 are arranged on either side of the central conveyer 19 so that each processing instrument's 14 local mover 26 has access to a single respective central mover access nest 32. The processing instrument 14 positions are staggered (also known as fixed pitch) or otherwise arranged so that all processing instrument 14 movers 26 may simultaneously access their central mover access nests 32. Therefore, the spacing between the modules 16 (and associated dedicated movers 26 and instruments 14 along the length of the central conveyer 19 is done at a fixed pitch, such that the individual movers 26 can simultaneously pick up and drop their respective samples 12 between their respective nest 32 of the conveyer 19 and the respective nest 30 of the instrument 14. It is recognised that the fixed pitch is such that there is no interference in motion between the adjacent movers 26 of the robotic system 10.

Figure 4:
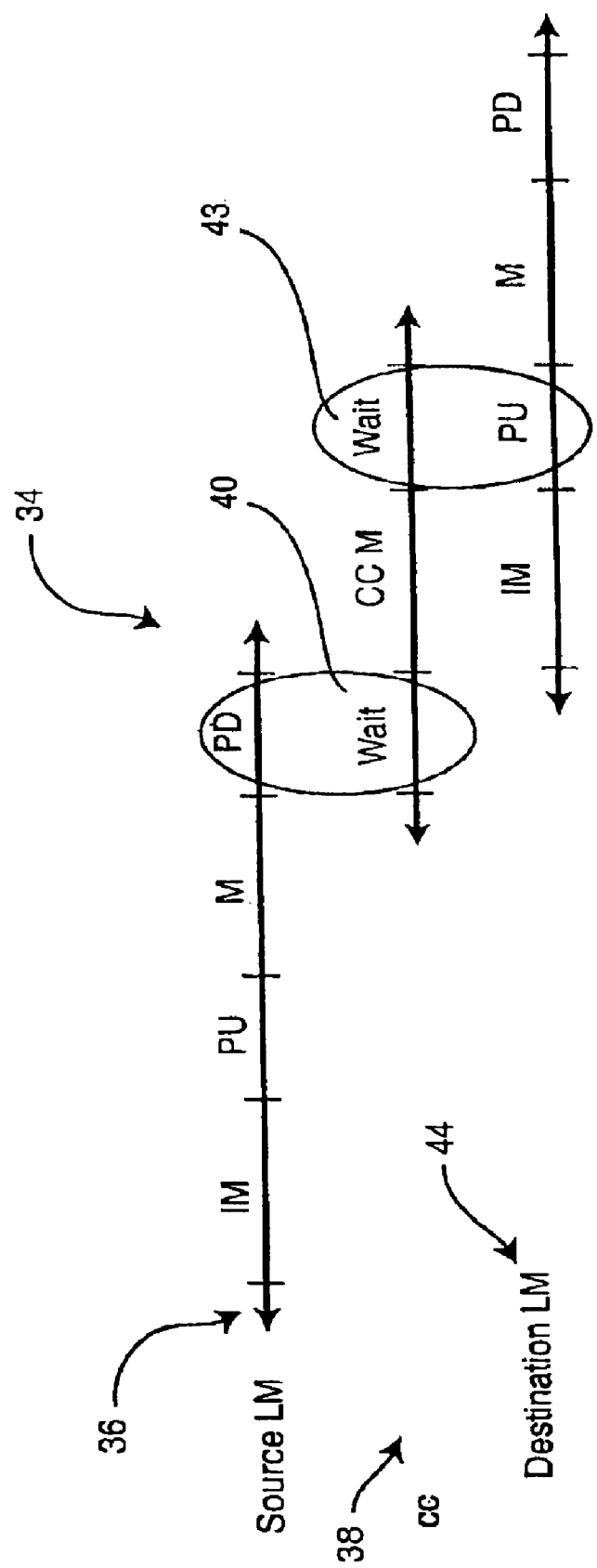
FIG. 4 provides a timeline for a single nest-to-nest move of the system of FIG. 3.

Referring to FIGS. 3 and 4 presents a time-line sequence 34 of the steps required to move the object (sample 12 of FIG. 1) from the access nest 30 of one processing instrument 14 (for example instrument 2) to the access nest 30 of another processing instrument 14 (for example instrument 4). A source sequence 36 (for instrument 2) has the respective local object mover 26 perform an initial move (1M to the processing instrument 14 access nest 30 and picks up (PU) the object to be moved. The local mover 26 (of instrument 2) then moves to just above its respective central conveyer 19 access nest 32 by move M. At this point, the central conveyance (CC) sequence 38 must be stopped (denoted by Wait 40) while the local mover 26 of instrument 2 puts down (PD) the object in the adjacent access nest 32. The conveyer 19 now moves rapidly to position (denoted by CCM in sequence 38) the object in the nest 32 at the position of the destination local mover's 26 access nest 32, adjacent to instrument 4. At this point the conveyer 19 must stop (Wait 43) to allow the destination local mover 26 of instrument 4 to Pick Up (PU) the object from its access nest 32 for sequence 44. The destination local mover 26 may then carry on in the sequence 44 to place the object in the destination processing instrument's 14 access nest 30 while the conveyer 19 is free to be used for other purposes.

Figure 5:
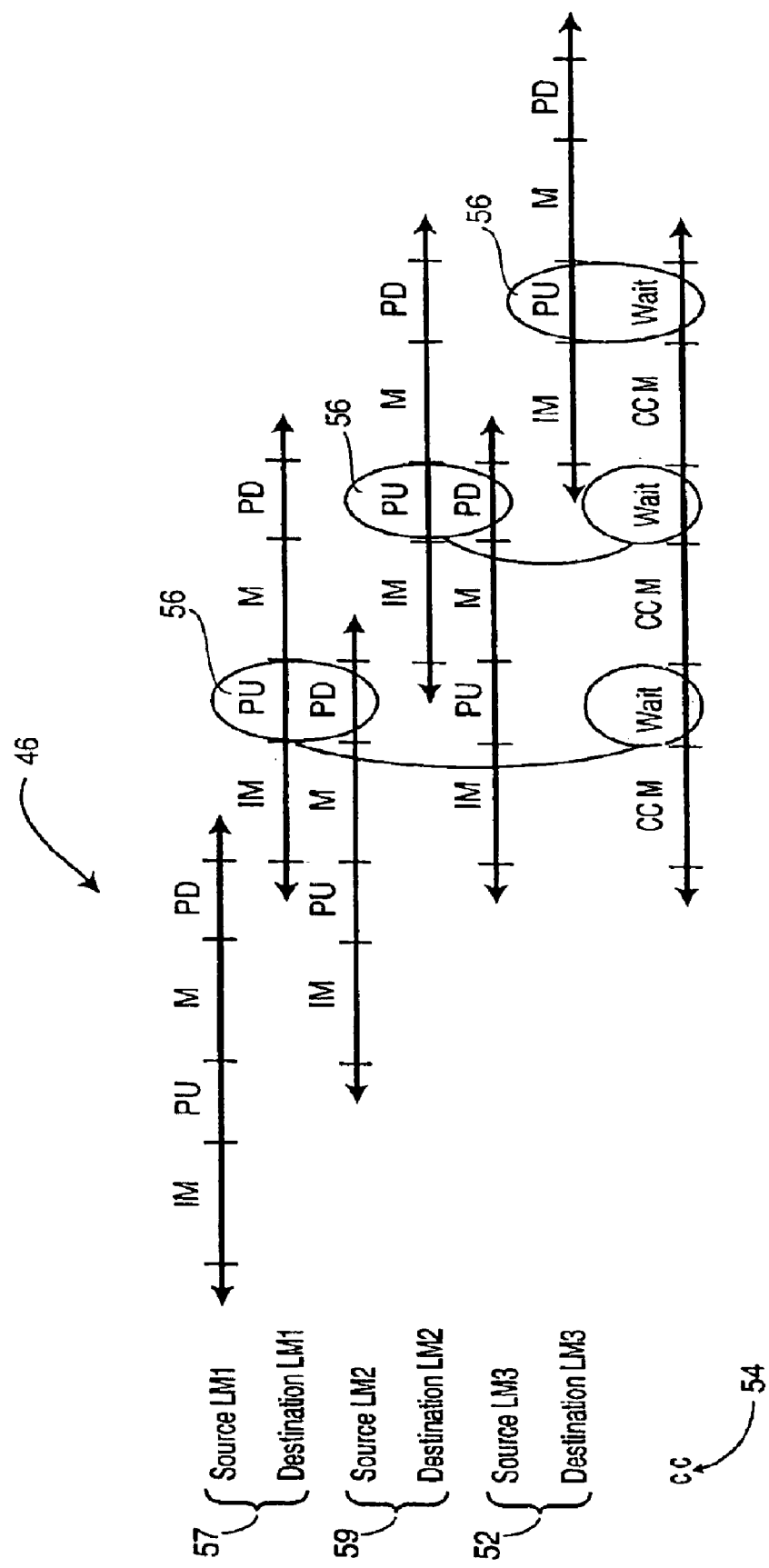
FIG. 5 provides a timeline for a multiple nest-to-nest move of the system of FIG. 3.

Similarly, referring to FIG. 5 shows a timeline sequence 46 for motion of multiple objects between several processing instruments 14. i.e movement according to simultaneous local sequences 57, 59, 52 in conjunction with central sequence 54 of the conveyer 19. Note that the only time that the central conveyer 19 is not able to move is when it is waiting for Pick Up or Put Down operations, as indicated by the circled regions 56 of the coordinated sequence 46. Accordingly, the system 10 can move multiple samples 12 between the individual instruments 14 and central conveyer 19. The system 10 (see FIG. 2) during operation allows for an overlapping architecture, whereby the different local movers 26, either dedicated to each module 16 or located on the central conveyer 19, are able to simultaneously coordinate their movements with one another and with the operation of the central conveyer 19, as further described below with regard to FIGS. 12 and 19. In effect, a hierarchical structure of the robotic system 10 is enabled, with the central conveyer 19 considered the root mover and the associated local movers 26 as a series of sub-mover systems. Each of the movers 26 can interact simultaneously with the central mover or conveyer 19, thereby facilitating parallel processing of the samples 12 by the instruments 14, as the samples 12 move from one location to any other location of the backbone 18, such as in a bi-directional and somewhat random fashion.

For example, it should be noted that the robotic system 10 can facilitate many individual component motions of the local movers 26 and the central conveyer 19 to occur at the same time. For example, the Pick Up (PU) and Put Down (PD) operations clearly may overlap, and the Initial Move (IM), instrument 14 access nest 30 Pick Up (PU) and local mover 26 Move (M) operations can occur simultaneously with the operation of the central conveyer 19.

Figure 6:
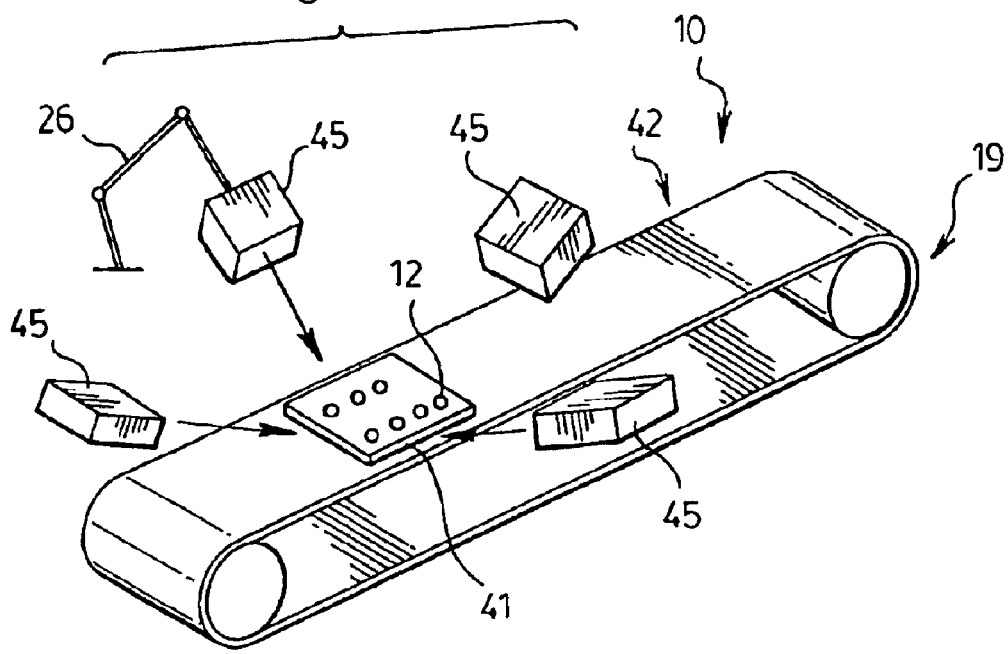
FIG. 6 shows a perspective view of on belt processing for the system of FIG. 1.
Figure 7:
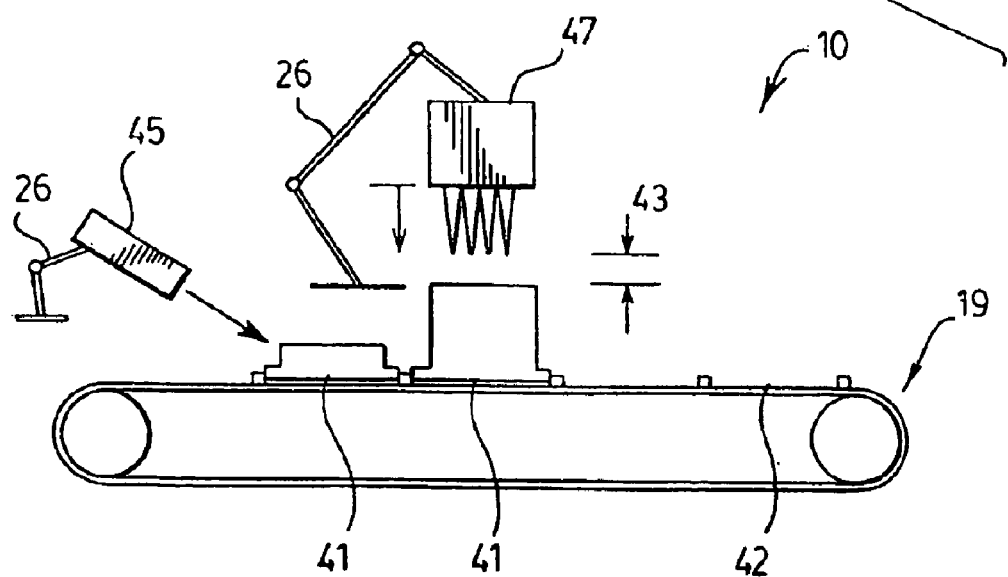
FIG. 7 is a side view of the system of FIG. 6.

Referring to FIGS. 6 and 7, another variation of the central conveyer 19 is to allow "On-Belt Processing" operations to be performed on the samples 12 while still on the conveyer 19. On-belt processing occurs when an active operation is applied to a plate 41, such as a micro titration plate or other container, without moving the plate 41 from the belt 42 of the conveyer 19. In a preferred embodiment, the instrument 47 of the module 16 (not shown for clarity) applying the operation normally maintains a position clear of any plate 41 moving on the belt 42, by maintaining a safe height determined by the distance 43 between the lowest hanging physical feature of the instrument 47, and the height assumed by the tallest plate 41 on the belt 42. It is understood the instrument 47 can be manoeuvred potentially by a local mover 26.

Under such an embodiment, it may or may not be necessary to provide additional fixturing to the plate 41 once it is positioned at the active location adjacent to the instrument 47, depending upon the type of operation being conducted. An example of a low-accuracy application could be provided by a bar code reader 45, where the bar code reader 45 reads a barcode applied to any of the four sides of the plate 41. In such a case, the normal positional accuracy and repeatability of the belt 42 can be sufficient to allow relatively error-free operation without external aids. It is recognised that the reader 45 and the instrument 47 can be associated with separate modules 16 (see FIG. 1).

Figure 8:
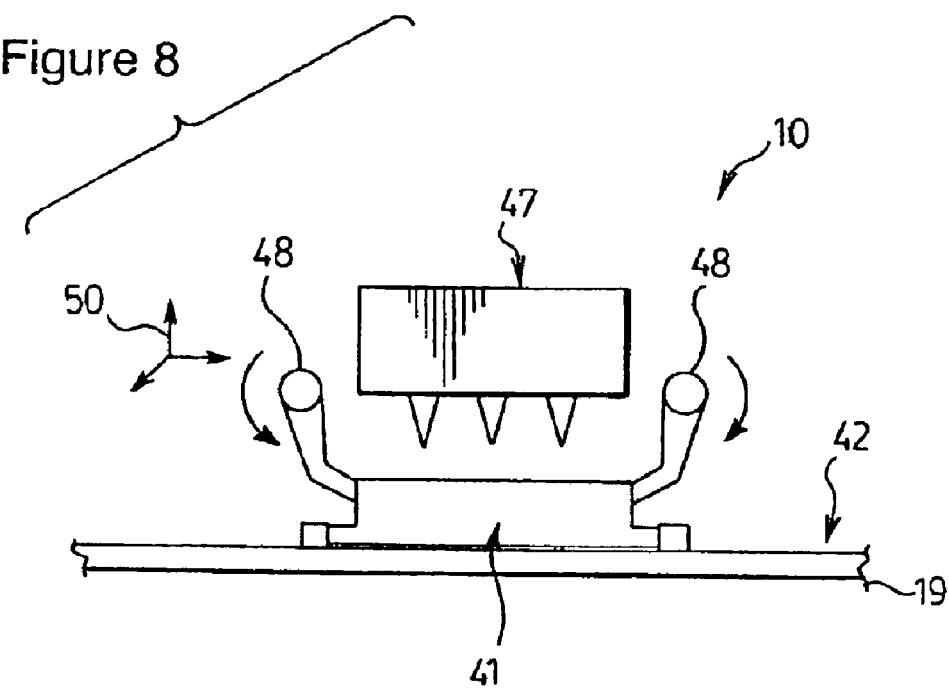
FIG. 8 is an alternative embodiment of the system of FIG. 6.

Referring to FIG. 8, an example of a higher precision application could be provided by a 384-tip dispensing head instrument 47 that requires a firm fixturing of the plate 41 so as to not allow the tips of the instrument 47 to collide with the plate 41 due to an inaccurate location of the individual wells of the plate 41 with respect to the head instrument 47. In such a case, a retractable fixture mechanism 48 is used to secure the position of the plate 41 in three coordinate axes 50 while the dispensing head of the instrument 47 operates on the plate 41. It is recognised that the fixture mechanism 48 and the head instrument 47 are associated with the same module on the same side of the conveyer 19 or associated separately with respective opposing modules on either side of the conveyer 19 (see FIG. 1).

Figure 9:
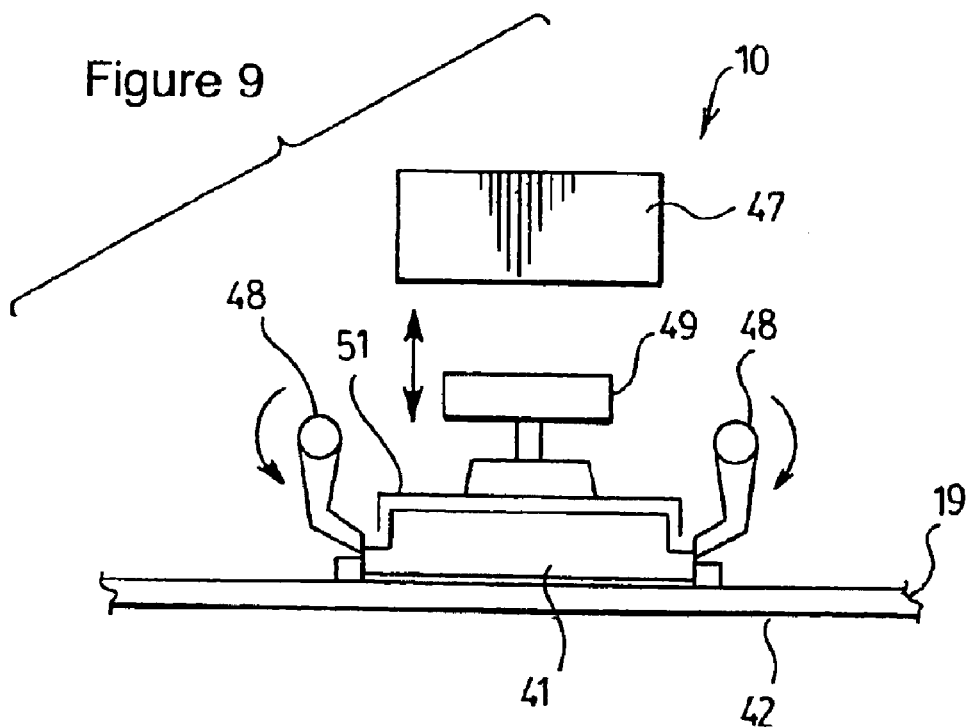
FIG. 9 is an alternative embodiment of the system of FIG. 8.

Referring to FIG. 9, in another high-precision example, a plate delidder 49 removes and replaces lids 51 on the plates 41, which are then carried by the belt 42 to the next active location. In such a case, the retractable fixtures 48 secure the location of the plate 41 so that the precise operation of lid 51 replacement by the delidder 49 can be conducted with minimal risk of failure, due to the potential collision of the plate lid 51 and the plate 41 through a misalignment of the lid 51 and the plate 41. This misalignment can be caused by the normal positional repeatability of the belt 42 being greater than the tolerance between the lid 51 and plate 41 sizes. Further, it is recognised the delidder 49, fixture mechanism 48, and head instrument 47 can all be associated with the same or opposing modules, as desired. In addition, it is recognised the plate 41 is brought to the active location by the system 10, whereupon the belt 42 stops, and the action is conducted by the appropriate instruments 47. A controlling software of the system 10 (for example associated with a controller of the central backbone 18 can govern the actions of the individual components (47, 48, 49), associated with the respective modules 16, such that the belt 42 is in use while the active operation is being conducted, and it is not permitted to perform any motion until the operation is signalled as completed. It is recognised that communication between components 47, 48, 49 and the controller can be accommodated by direct connections between the modules 16 and the backbone 18 through respective connection interfaces, as further described below.

Figure 10:
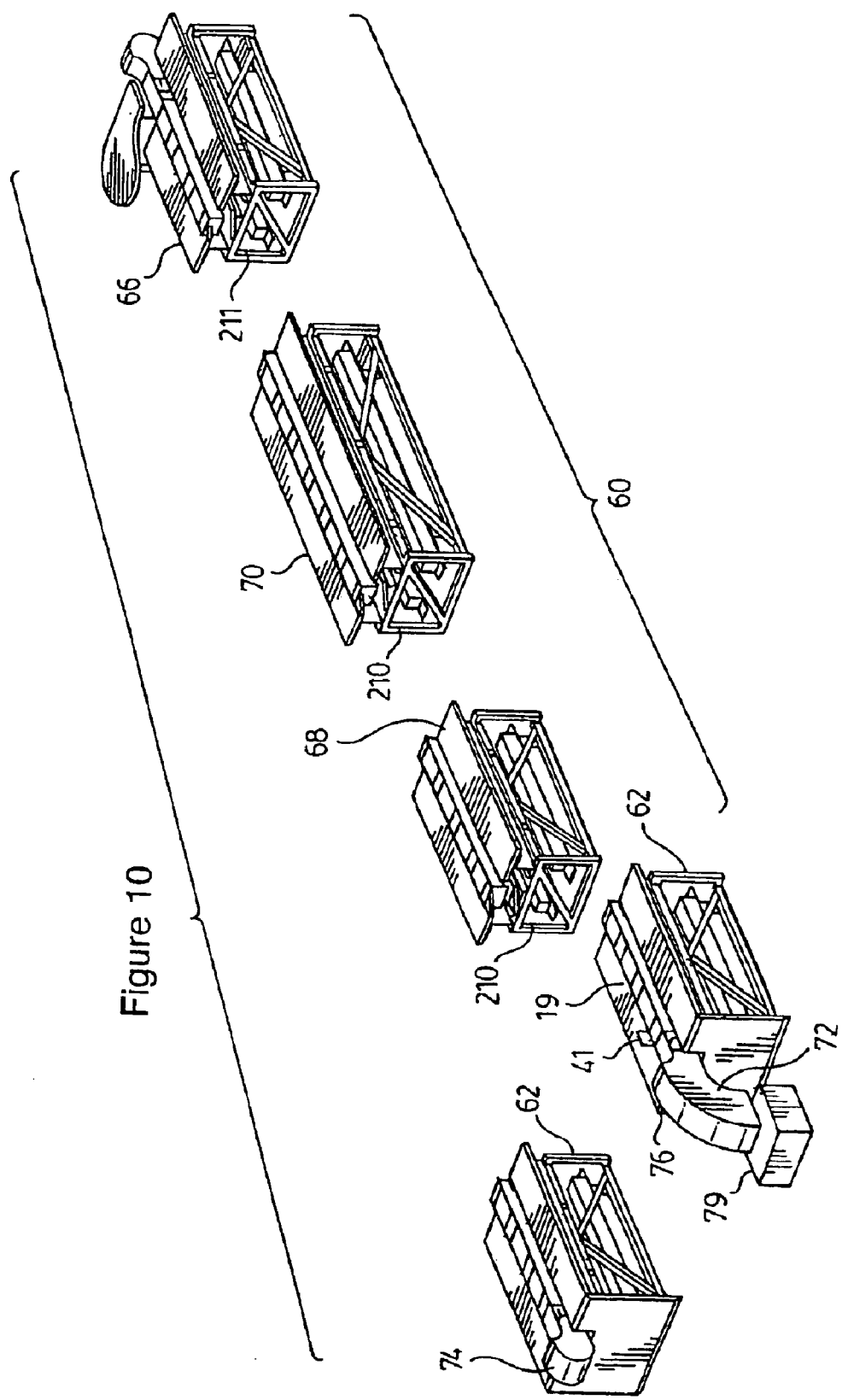
FIG. 10 is a modular and extensible conveyer embodiment of the system of FIG. 2.

Referring to FIG. 10, the central backbone 18 (also referred to as a linear plate transport) can consist of, for example such as but not limited to, three separate components 60 with two optional components 68, 70. The components 60 include a Motor Section 66, an 800 mm Insert Section 68, and an 1200 mm Insert Section 70, and the Idler Section 62. The Idler Section 62 has a plate catcher 72 option, or a plate chute 74 option. It should be noted that the options 72, 74 can be add-on features and may not be required for operation of the backbone 18 containing the components 60. The backbone 18 can also be modular and extensible due to conveyer connection interfaces 210 for operationally interconnecting the components 66, 68, 70, 62 with one another. The interfaces 210 can accommodate such as but not limited to, electrical, mechanical, and resource continuity between the components 62, 66, 68, 70 when coupled to one another.

Figure 11:
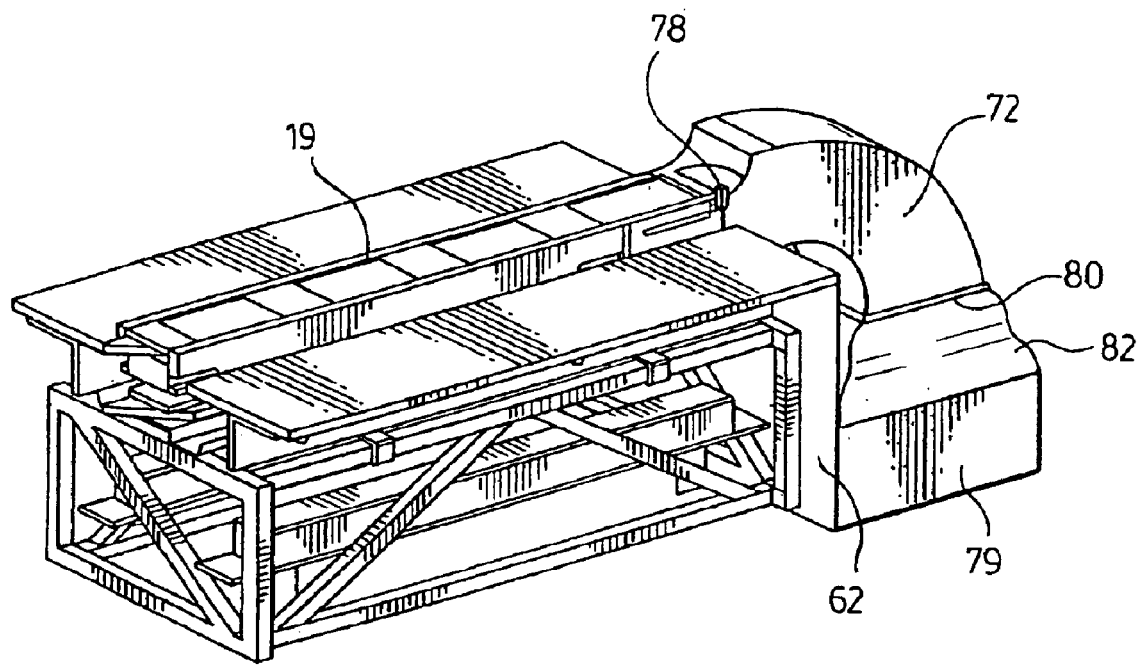
FIG. 11 shows an optional section of the conveyer of FIG. 10.

Referring again to FIG. 10, the plate chute 74 is a device used to dispose of unwanted plates 41 directly from the conveyer 19. The chute 74 attaches to an idler end 76 of the conveyer 19, as seen in by means of the attachment tabs 78 seen in FIG. 11. The chute 74 is curved so that plates 41 can easily slide into a disposal bin 79 located below while inhibiting the plate's 41 contents to become airborne. The chute 74 has a rim 80 about its lower edge, so that a cover 82 attached to the disposal bin 79 can be affixed to the rim 80 without sliding off. The cover 82 is used to contain splashes from the waste plates 41 dropping into the disposal bin 79.

Figure 12:
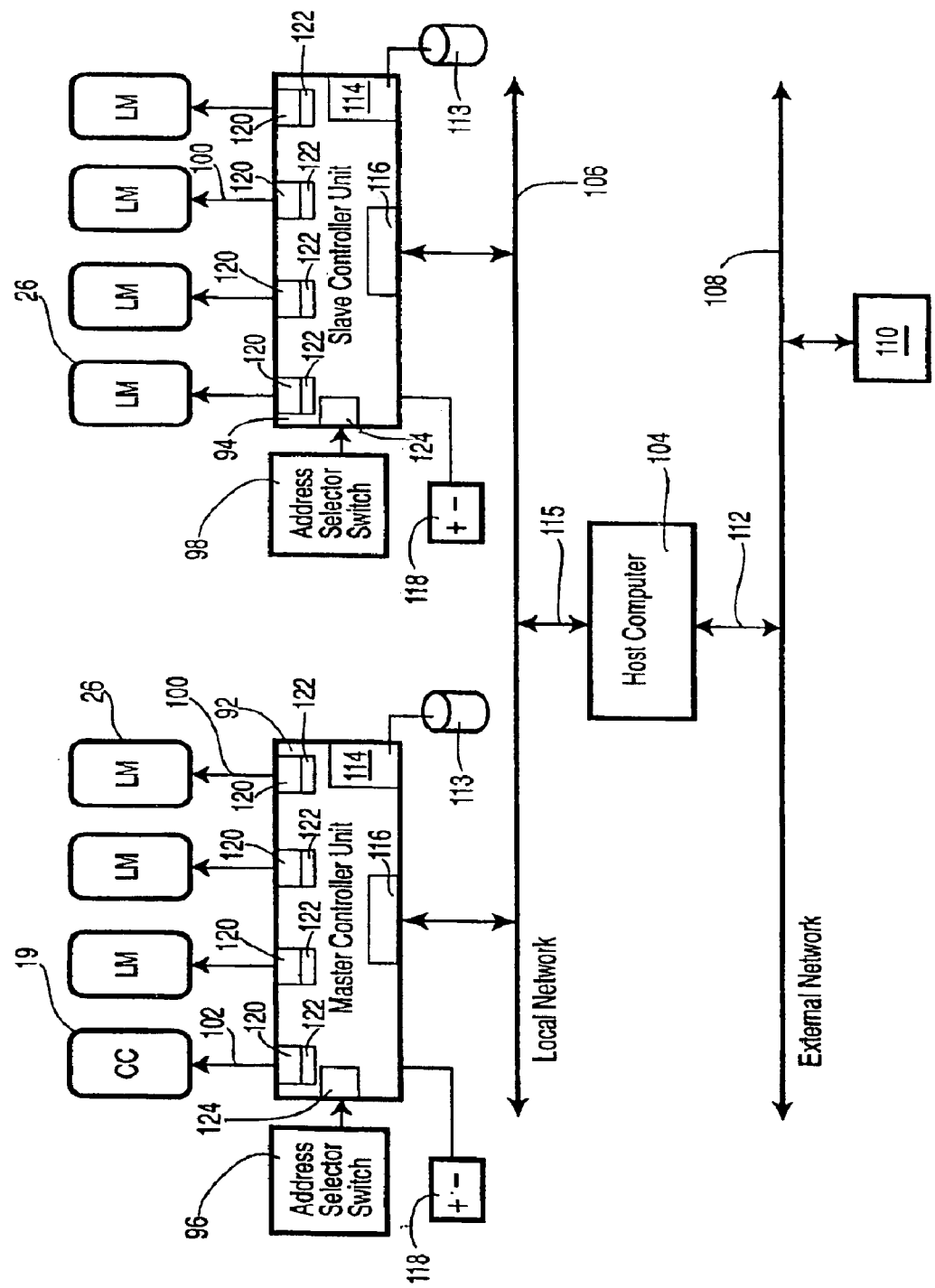
FIG. 12 shows a mover controller network setup for the system of FIG. 1.

Referring to FIG. 12, a mover control configuration 90 for a laboratory embodiment of the automation system 10 (see FIG. 1) has, such as but not limited to, two mover controllers 92 "Master Controller Unit" and 94 "Slave Controller Unit", which can be largely identical devices. For example, the primary difference of the controllers 92, 94 is a setting of an "Address Selector Switch" 96, 98 attached to each controller 92, 94. The Master Controller 92 has the selector 96 set to a predetermined code to signify the master designation (for example the numeral "0"). Accordingly, there may then be one or more slave controllers 94 which have unique, non-zero numerals selected as their address switches 98 to signify slave designations (for example the numerals "1", "2", etc. . . . ). It is recognised that some system 10 arrangements can have no slave controllers 94, thereby using only a single controller 92.

Referring again to FIG. 12, each controller 92, 94 may control up to a fixed number of local mover devices (LMs) 26 through individual ports 100. A first mover control port 102 on the master controller 92 typically controls the central conveyer 19 (otherwise known as the linear plate transporter or LPT). Further, the overall operation of the robotic system 10 (see FIG. 1) by the mover control configuration 90 is monitored by a Host Computer 104, which communicates with the various controllers 92, 94 via a Local Network 106. This Local Network 106, such as but not limited to a standard 10BaseT ethernet network, is used for controlling the system 10. For example, there may be no direct connection between the Local Network 106 and any external network 108, such as but not limited to the Internet.

Referring again to FIG. 12, it is understood that a plurality of host computers 104 could be monitored by a central control system 110 connected to the external network 108. The Host Computer 104 may be configured with two separate network interfaces, namely 112 and 115, to the external 108 and local 106 networks respectively, should it be desired that the host computer 104 be able to communicate with other host computers (not shown), possibly over a building intranet or the Internet. This separation of the Local network 106 and the External Network 108 can be beneficial in order to hinder interference of network traffic on the External Network with the operation of each independent robotic system 10. Further, the separation of the networks 106, 108 also hinders interference of traffic from each of the robotic systems 10 interfering with communications on the External network 108. It is understood that each of the host computers 104 could be responsible for monitoring respective robotic systems 10.

Referring again to FIG. 12, the controllers 92, 94 can be small stand-alone computers with the following equipment, such as but not limited to: a) local storage 113 for storing operating software required for the controller's 92, 94 operation; b) an embedded computer 114 with adequate memory and processing speed for running the embedded software; c) a network communications device 116 for communicating with the host computer 104 and with other controllers 92, 94 over the Local Network 106; d) a power supply 118 for providing power to the various Local Movers 26 and Central Conveyer 19 attached to the controller 92, 94; e) a power switch disconnect 120 for allowing the mover power supplies 118 to be switched on and off (either in whole or in part) to enable and disable the various attached movers 26 together and/or separately; e) individual communication signalling devices 122 for sending commands to a plurality of servo motor sets (not shown), each set operating the axes of each of the local movers 26 and/or the conveyer 19 (as a whole or as components 22, 24—see FIG. 2) attached to the respective controller 92, 94; and f) a digital reader 124 for sensing the numeral selected on the address selector switches 96, 98. The digital readers 124 help the embedded software of the controllers 92, 94 to determine if the controller 92, 94 is a Master Controller or if it is a slave controller, and to determine which address should be used for network communication to the host computer 104 through the communications device 116. For example, the address selector switch 96, 98 may be set to one of 16 possible values, 0 to 15. It should be noted that the communication devices 122 are preferably individually linked to the respective local movers 26 and/or conveyer 19.

Referring again to FIG. 12, the above presented hierarchy of control of the robotic system 10 can have several advantages. For example this hierarchy of control can be between the central computer system 110, host computer 104, the master and slave control units 92, 94, and the local control and signalling units 122. Since each mover 26 has its own communication device 122 connecting it to its respective controller 92, 94, and to its respective controlling process on its respective controller 92, 94. Therefore, operation of one mover 26 may not affect or interfere with operations of any other controllers 92, 94 and their associated controlling processes. This use of respective communication devices 122 and separate controlling processes can also help accommodate modular engagement and disengagement of the respective modules 16 (see FIG. 1), as further explained below. The number of movers 26 that can be attached to one controller 92, 94 is set to a predefined number, for example four, to help manage the cost and complexity of the controller's 92, 94 circuitry. The limited number of local movers 26 per controller 92, 94 also helps to provide for the controller's 92, 94 embedded computer 114 having adequate processing power to control each mover 26, and by executing its individual control process. For example, it can be critical in some robotic system 10 arrangements that each mover 26 be given sufficient attention by the embedded computer 114, during operation of the appropriate time line sequencing 34, 46 (for example see FIGS. 4 and 5), or else time-critical events like initiating the motions of multiple axes of the movers 26 and/or conveyers 19 can fail to occur at the right moment, thereby potentially causing undesirable collisions.

Figure 19:
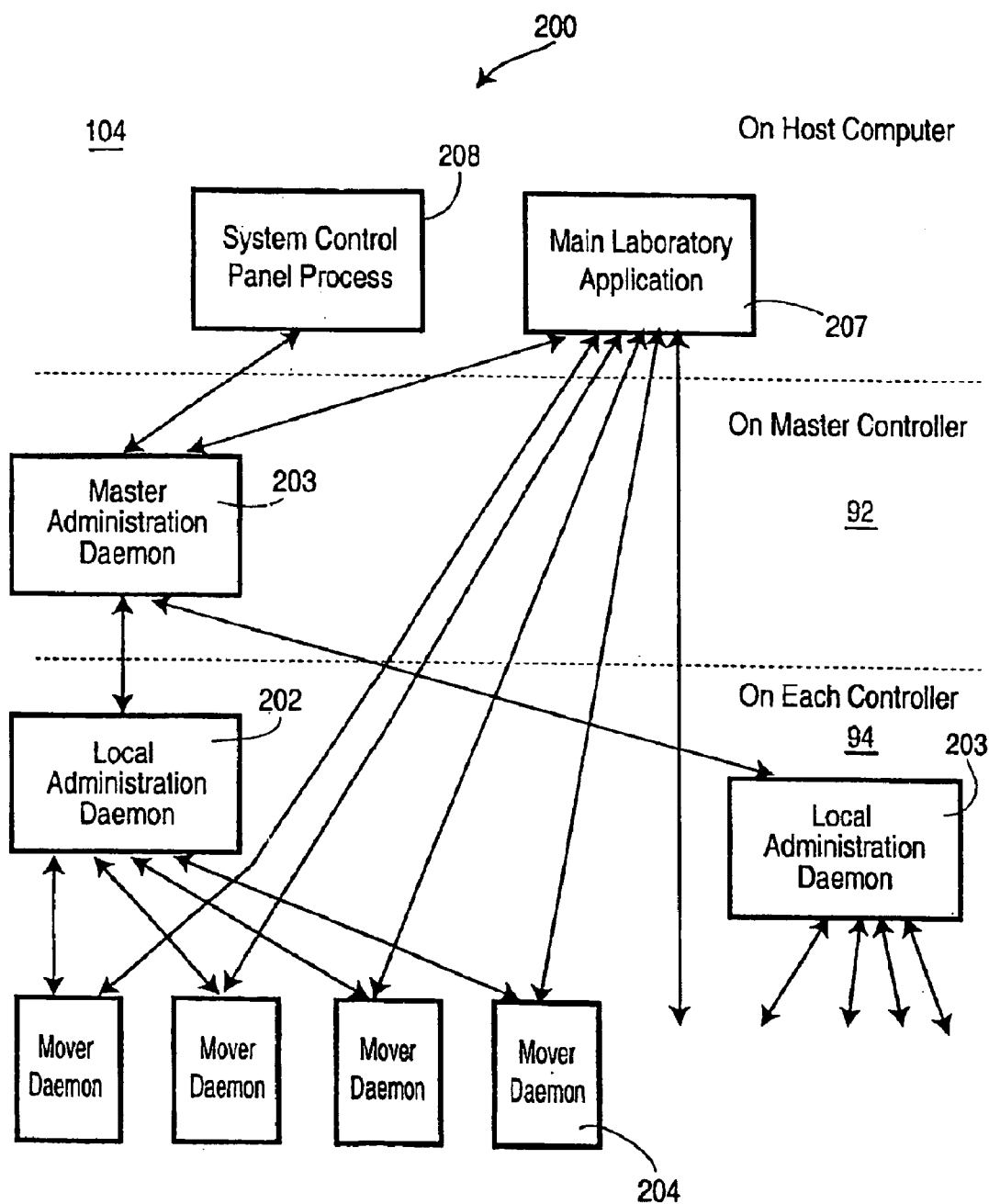
FIG. 19 is a diagram of a distributed control system of the robotic system of FIG. 1.

Referring to FIGS. 12 and 19, the operation of the set of mover controllers 92, 94 is controlled by a hierarchy of parallel control processes (programs) 200, which reside partially on the Host Computer 104 and partially on the Master Controller 92, and partially on each Slave Controller 94. FIG. 19 shows the hierarchy of control programs 200.

Referring again to FIG. 19, each controller 92, 94 (including the Master Controller) has a Local Administration Daemon 202 which provides controller status information services to other processes by means of the controller's network interface 102. The Local Administration Daemon 202 is also responsible for starting up and shutting down Mover Daemons 204, which control the various local movers 26 and central conveyer 19. Each attached mover 26 is controlled by its own dedicated process called the Mover Daemon 204. The Mover Daemons 204 provide motion control services to the Administration Daemons 202 and to laboratory automation applications 207 on the host computer 104. The automation application 207 is used to operate the modular robotic system 10 (see FIG. 1). In addition to the Administration Daemon 202 and the set of Mover Daemons 204, the Master Controller 92 has a Master Administration Daemon 203 process that provides entire system 200 start-up and shut down services, emergency stop control services, and whole system 200 monitoring services to processes on the Host Computer 104. A Control Panel program 208 on the Host Computer 104 allows the user to start up, shut down and monitor the system 200 and therefore the operation of the robotic system 10.

It is noted that the purpose of each process 202, 203, 204 on each controller 92, 94 can be well-defined and of very limited scope; whereby each process 202, 203, 204 has a sharp, or well-defined interface. This well defined interface allows for partitioning of the various functional responsibilities of the system 200, such that the processes 202, 204, 206 have distinct yet compatible controlling operations. For example, the intent of this arrangement is to help ensure that all time-critical tasks of the robotic system 10 can be performed in a timely fashion, mainly independent of the operation of the Host Computer 104. Thus, software or hardware malfunction or user errors on the Host Computer 104 may not affect the safe and timely operation of the embedded computers 114 on the Controllers 92, 94. Another potential benefit of having a multiplicity of well-defined control processes or daemons 202, 203, 204 is that the complexity of each control process can be kept to a manageable level, helping to simplify software maintenance.

Referring again to FIGS. 12 and 19, the central conveyer 19 and multiplicity of movers 26 are controlled via the mover control hierarchy 90 or network. Each controller 92, 94 can communicate on an Ethernet protocol, and controls a multiplicity of movers 26, with for example a limit of 4 movers 26 per controller 92, 94. Each robotic system 10 can be outfitted with the "master" controller 92 and several "slave" controllers 94. Each of the controllers 92, 94 can have safety circuitry for Emergency stop control.

Figure 13:
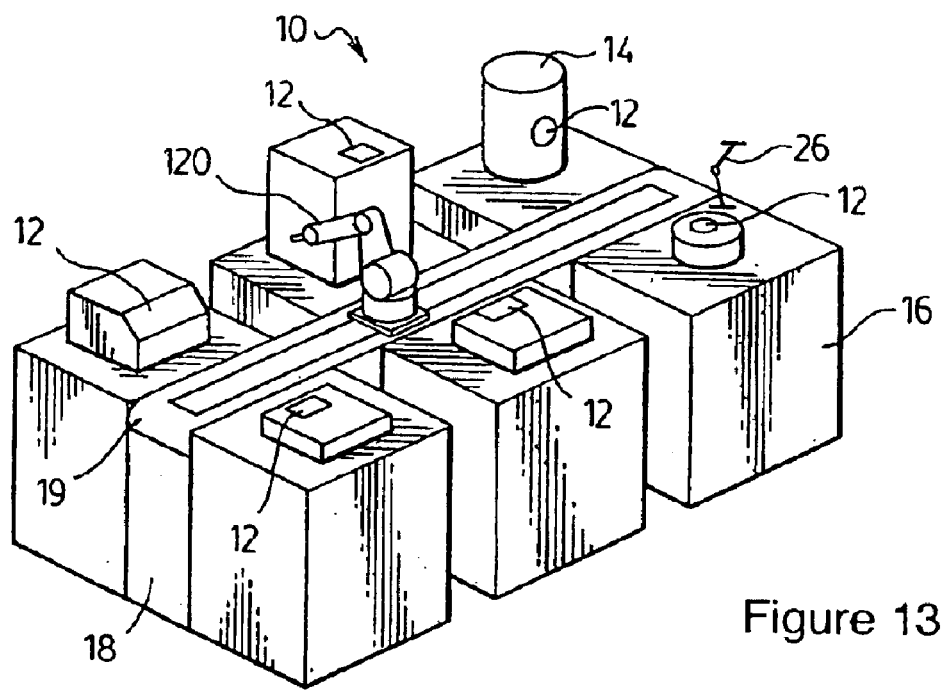
FIG. 13 is a further embodiment of the system of FIG. 1.

Referring to FIG. 13, the modular architecture of the robotic system 10 can also accommodate the use of a central mover 120 affixed on the conveyer 19. The central mover 120 can have the ability to accept and deliver the sample(s) 12 directly between the process instruments 14. The design of this Track mover type can be modular as well, and can allow the modular extension of the robotic system 10, as further discussed below. This type of central mover 120 can be of interest when less automation friendly instrumentation has to be accessed, or the loading areas of the instruments 14 are restricted. The method steps for processing the samples using the central mover 120 can be broken into: a) random access sample 12 from a selected processing instrument 14 by the central mover 120; b) move central mover 120 between the modules 16 by the conveyer 19; c) load the sample 12 from the central mover 120 to the process instrument 14 directly; or load by the central mover 120 the local mover 26, if present, which then moves the sample 12 into the dedicated instrument 14. It should be noted in this embodiment that the central mover 120 is not dedicated to any one of the modules 16, rather it is shared there-between. Further, it is recognised that a connection interface (not shown) between the respective controller 92, 94 and the central mover 120 should accommodate the linear displacement potential of the conveyer 19, such that required operating resources (power, signalling, actuation fluid, etc. . . . ) of the central mover 120 remains uninterrupted for the duration of intended operation of the central mover 120.

Figure 14:
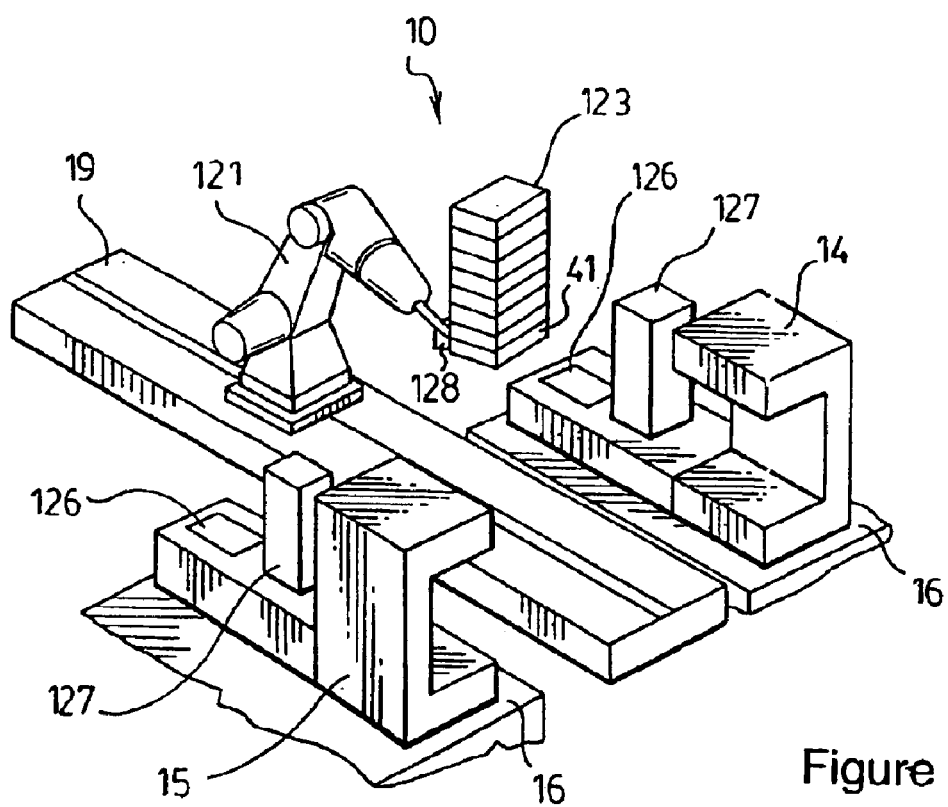
FIG. 14 is a stacking embodiment of the system of FIG. 13.

Referring to FIG. 14, a further embodiment of the central mover 121 is shown. One potential solution to processing bottlenecks associated with handling single plates 41 (see FIG. 6), with single articulated robots in laboratory automation systems 10, is to allow the robotic device such as the central mover 121 to carry more than one plate 41 (or other container) at a time and deposit this batch of plates 41 at individual instrument stations 14, 15. In such a system, the robotic device 121 can carry a number of plates 41 (such as but not limited up to 20 standard format plates 41 with a 3 kg payload) inside a stacking device 123 designed to nest into stationary stacking units 126 or docking stations. The stacking units 126 associated with respective modules 16 can be used to de-stack the individual plates 41 inside the stacking device 123, and then insert the individually selected plates 41 into the adjacent instrument 14, 15. After processing of the selected plate 41 by the respective instrument 14, 15, the processed plates 41 can then be re-stacked into their original stacking device 123 for subsequent retrieval by the central mover 121, or the processed plates 41 could be re-stacked into a different stacking device 127 with the similar physical characteristics to that of the original stacking device 123. Preferably, the central mover 120 operates by releasing the stacking device 123 at the appropriate module 16, so that the plate 41 selection, processing and re-stacking procedure can occur while the central mover 121 is moving another stacking device 123 full of plates 41 retrieved from a different module 16. The subsequent concurrent processing of stacking devices 123 can help provide for increased throughput and can be applicable for a range of applications, such as but not limited to drug screening.

Referring again to FIG. 14, central mover 121 uses a gripper 128 to carry the stacking device 123 from one arbitrary instrument 14 location to another instrument 15, along the conveyer 19. The gripper 128 can be designed to maintain a safe grasp of the stacking device 123, even when air pressure to the gripper 128 is lost due to failure, so as to help prevent dropping of the plate stack and the subsequent damage that could be caused by such a failure. The central mover 121 can be, for example, a 5 or 6 degree of freedom device affixed to the linear track conveyer 19. Preferably, the conveyer 19 can maintain a level configuration of the individual plates 41, when containing fluid samples, and can provide random orientation to place the stacking device 123 within the randomly positioned stacking units 126 associated with the modules 16. For example, there can be one of the stacking units 126 beside every active instrument 14, 15, wherein the purpose of the stacking units 126 is to move individual plates 41 from the deposited stacking device 123 to the adjacent instrument 14, 15 for processing. The stacking unit 126 can also be responsible for re-stacking the processed plates 41 into the original stacking device 123, or the different one 127, depending upon the assay. Optionally, the stacking unit 126 could move the processed plates 41 from the other stacking device 127 into the first stacking unit 123, thereby helping to preserve the order of the plates 41 within the stack.

Figure 15:
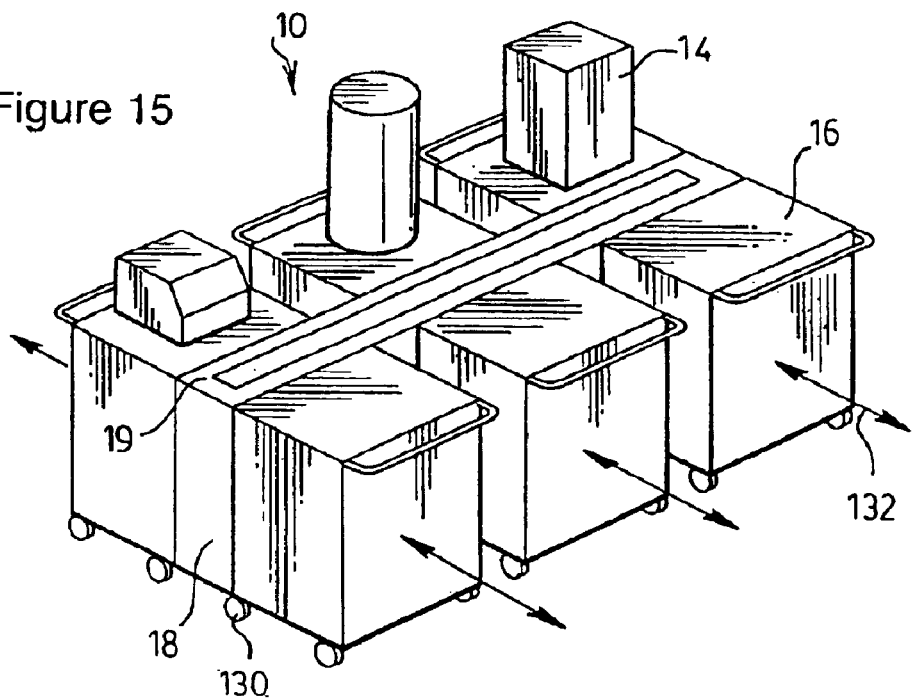
FIG. 15 shows a further embodiment of the modules of FIG. 1.

Referring to FIG. 15, the Modules 16 of the robotic system 10 can have rollers 130 to provide mobility to and from the central backbone 18, as indicated by arrow 132. The rollers 130 can facilitate the assembly, reconfiguration and attachment of the Modules 16 to the backbone 18. Further, it is recognised that other displacement mechanisms could be used, such as but not limited to wheels, castors, and other slider arrangements as is known in the art.

Figure 16:
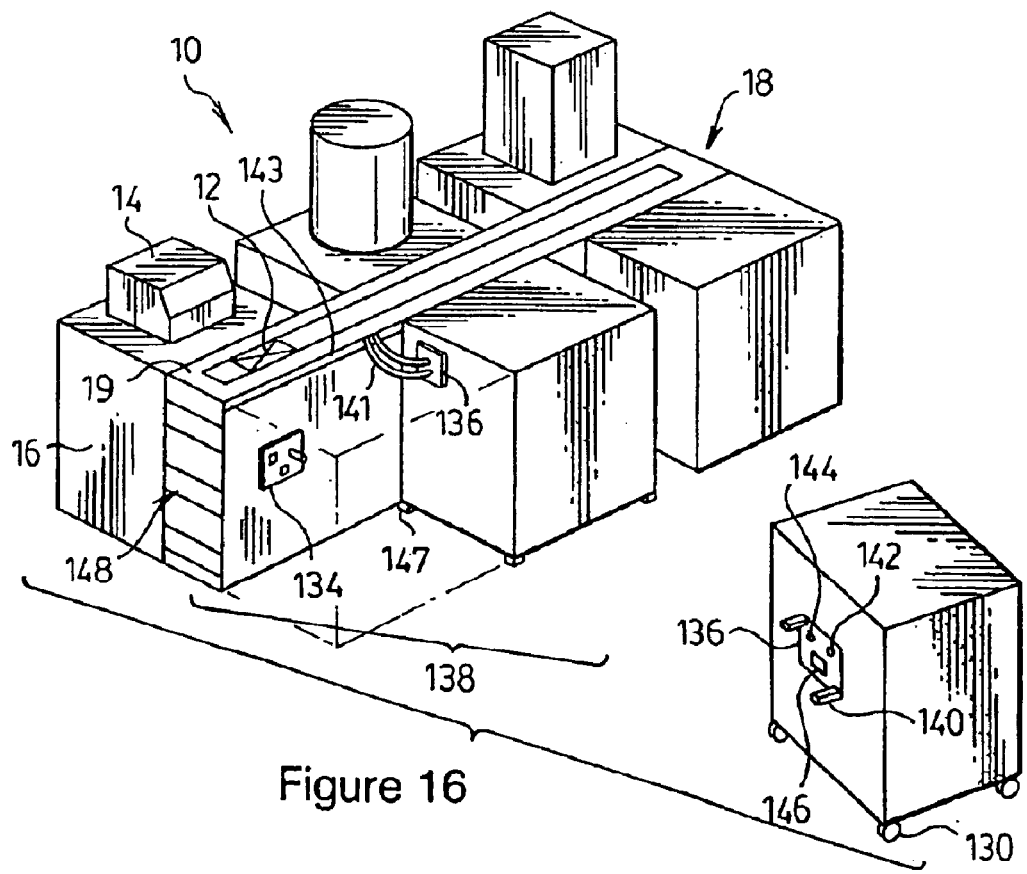
FIG. 16 shows an interface for the modules of the system of FIG. 1.

Referring to FIG. 16, the Modules 16 are releasably connected with the backbone 18 via a docking station or port 134. The docking port 134 operates as a universal connector interface 138 to allow for ready connection and disconnection of the Modules 16 from the backbone 18. The interface 18 is comprised of the docking port attached to the backbone 18 for each individual module 16, and respective module connectors 136. The cooperation of the respective ports 134 and connectors 136 for each module 16 provides for ready exchange and reconfiguration of the robotic system 10, as required by the process procedure of the samples 12. The interface 138 comprises a mechanical alignment device 140 between the backbone 18 and the module 16, an electrical connection 142, a pneumatic connection 144, and support of other supply resources 146 such as but not limited to air, water, and CO2. The design of the backbone 18 can also accept rack-mounted electronic equipment 148 on either end. Accordingly, the Modules 16 are hot-pluggable by means of the interface 138 to allow process instruments 14 to be connected or disconnected while the system 10 is running, whereby the individual interfaces 138 of the modules 16 provides for independent connection and disconnection between the modules 16 while the system 10 is in operation.

In an alternative embodiment, the connector interface 138 can include a manual connection of cables 141 coupled to the backbone 18, for attaching to the module connectors 136. Various cables 141 can be collected in a cable tray 143 located down the spine of the backbone 18. The cables 141 can include connections for electrical, pneumatic, and other desired supply resources 146. For example, the backbone connector is the set of cables 141 and the module connector is the receptor 136 adapted to connect with the cables 141. Otherwise, the module connector is the set of cables 141 and the backbone connector is the receptor 136 adapted to connect with the cables 141. The modules 16 can also be secured in position relative to the backbone 18 by fixed fasteners 147, such as but not limited to bolts.

Furthermore, referring to FIG. 12, the controllers 92, 94 and associated controlling software have the ability to recognise when old modules are removed 16 and new modules 16 are added to the backbone 18. For example, each module 16 type with respective instruments 14 can have unique identifiers that are communicated to the controllers 92, 94 to inform them of which modules 16 are either in or out of service in regards to the respective backbone 18 of the system 10.

Figure 17:
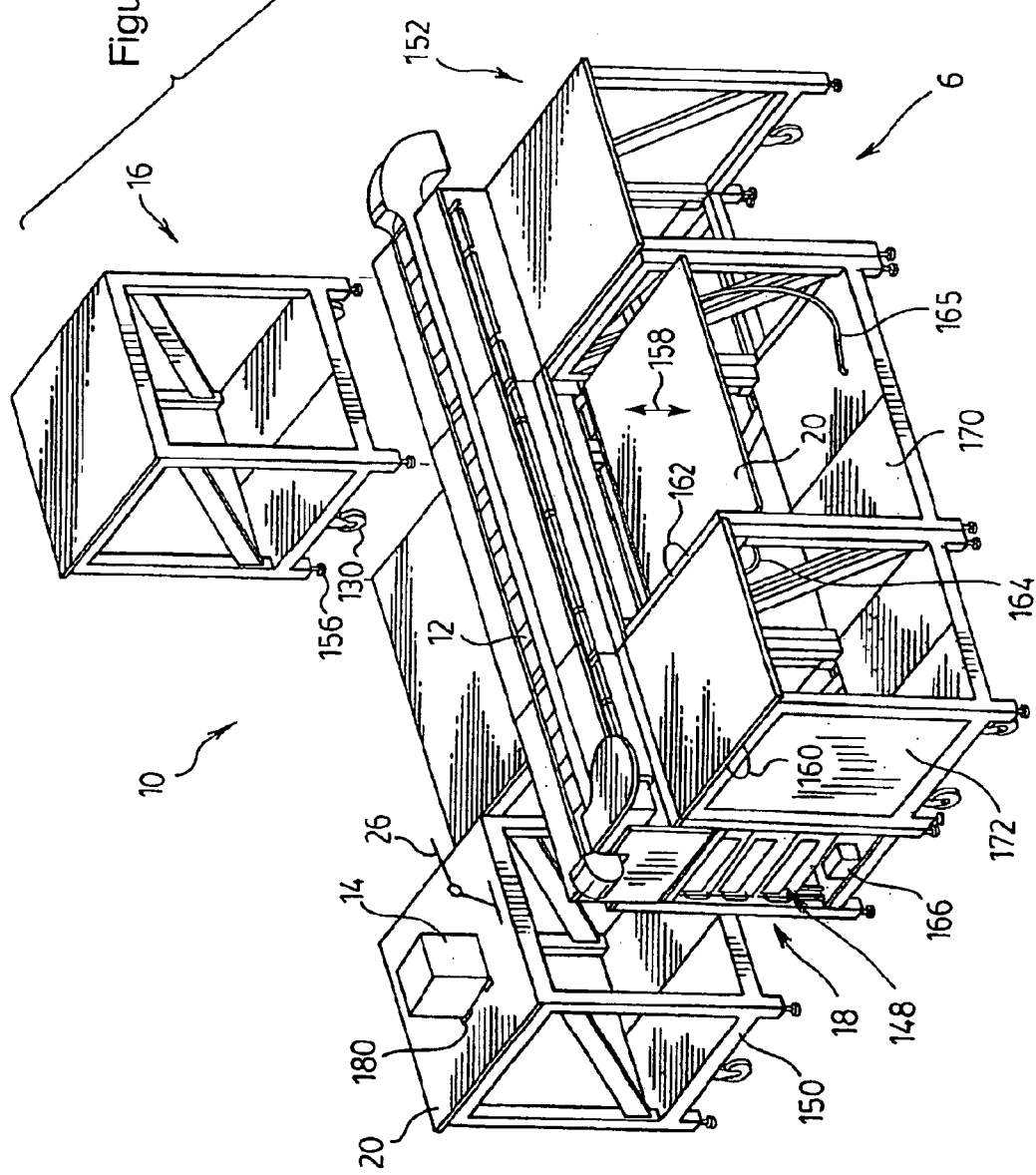
FIG. 17 is a perspective top view of a further embodiment of the system of FIG. 16.

Referring to FIG. 17, a variation of the above-described robotic system 10 is a series of frames 150 of "Modular tables"; whereby the assembly of Modular Tables represents a composite modular frame structure 152 that forms a continuous table surface when mounted to the backbone 18 (FIG. 4). The Modular Table frames 150 have both features of leveling feet 156 and rollers 130. If the system 10 has to be reconfigured, the feet 156 can be screwed into the table frame 150 so that the table rests on the rollers 130 and can be moved away from or towards the backbone 18. It should be noted the portability of the table frames 150 provides a series of self-contained modules 16, thus allowing the use of the modules 16 in either stand-alone or in the interconnected mode with the backbone 18, if desired.

Referring again to FIG. 17, the individual modular table frames 150 are comprised of several independent table modules 16 that can be combined into many different configurations or can be used on their own. In addition to the ability to configure groupings of the table frames 150 to suit an application, there are many other features and options that add to the overall flexibility and configurability of the robotic system 10. For example, reconfiguration of the table frame 150 groupings, representing an assembly of modules 16, is possible because each module 16 is preferably completely self-supporting and structurally independent from those around it. Therefore, as the application for the robotic system 10 changes, each module 16 can be moved in relation to the backbone 18 to reconfigure the overall table structure 152. For example, the frame 150 of each module 16 can be attached to other modules 16 to make a smaller mini-system 10, or can be completely removed and used as a stand-alone workcell.

Referring again to FIG. 17, each module 16 also has the option of sinking its respective tabletop surface 20 up to for example 6" as indicated by arrow 158. This allows the instruments 14 and movers 26 to be positioned at an optimum height with respect to the conveyer 19, as well as to provide for instruments 14 with varying heights of loading nests 30.

Referring again to FIG. 17, the power distribution of the robotic system 10 has also been designed in a modular fashion. For example, each table module 16 contains a pre-wired power bar, with a standard power input 160 on one end and an output 162 on the other, consequently providing for each module 16 to be "daisy-chained" to the adjacent module 16 to form a single circuit. Another option is that each module 16 could be routed by a cable 165 back to a main supply 166 on the backbone 18 so as to remain as an independent circuit. Therefore, as power requirements change for the system 10, the power distribution for the modules can be re-configured to accommodate.

Referring again to FIG. 17, another feature of the frame 150 of the modules 16 is the ability to remove a lower shelf 170 and support brace from underneath the module 16. This removal allows an end user to make room for larger pieces of equipment that can sit under the table 20, or provide a clear area to wheel-in such things as waste and reagent containers. Further note, each end of the backbone 18 has rack mount spacing so that the rack mount equipment 148 can be secured within the robotic system 10. Referring again to FIG. 17, adjustable shims 180 can be situated between the instruments 14 and the table surface 20 to help provide a common datum for transfer of the samples 12 between the conveyer 19 and the modules 16 by the mover 26.

Figure 18:
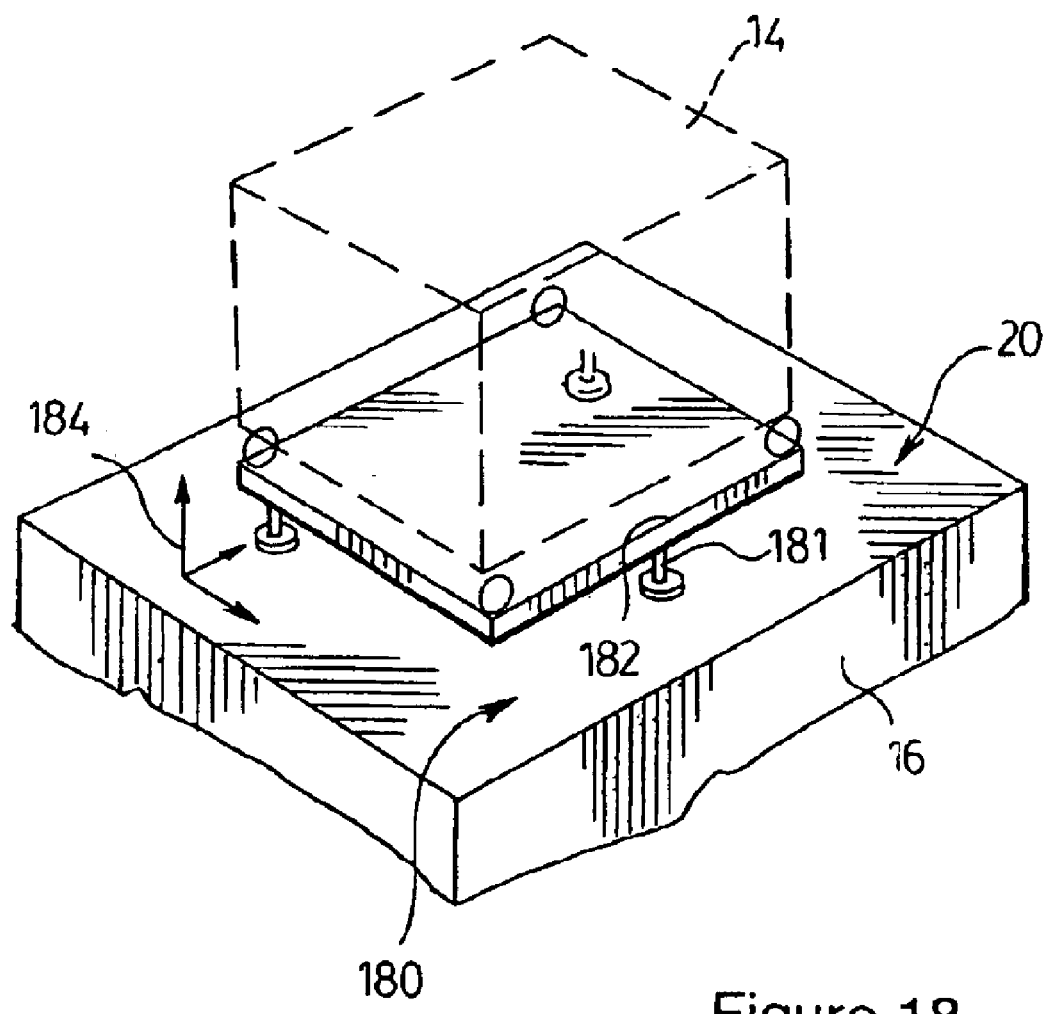
FIG. 18 is a perspective view of shims of FIG. 17.

Referring to FIG. 18, the instrument 14 (shown in ghosted view for clarity) is positioned on the table 20 of the module 16 by shims 180. One embodiment of the shims 180 is a series of adjustable bolts 181 securable in respective oversized holes 182 (i.e. the diameter of the bolt 181 is smaller than the diameter of the hole 182. Accordingly, each of the bolts can be secured in a six degree of freedom coordinate system 184, by respective nuts (not show for clarity). Accordingly, the shims 180 are situated in a triangular orientation such that the instrument 14 can be adjusted in position in relation to the table 20. Referring again to FIG. 17, the position of the instrument 14 can be calibrated in respect to the fixed position of the module 16, movers 26, and conveyer 19 when the modules 16 are releasably secured to the backbone 18.

Figure 20:
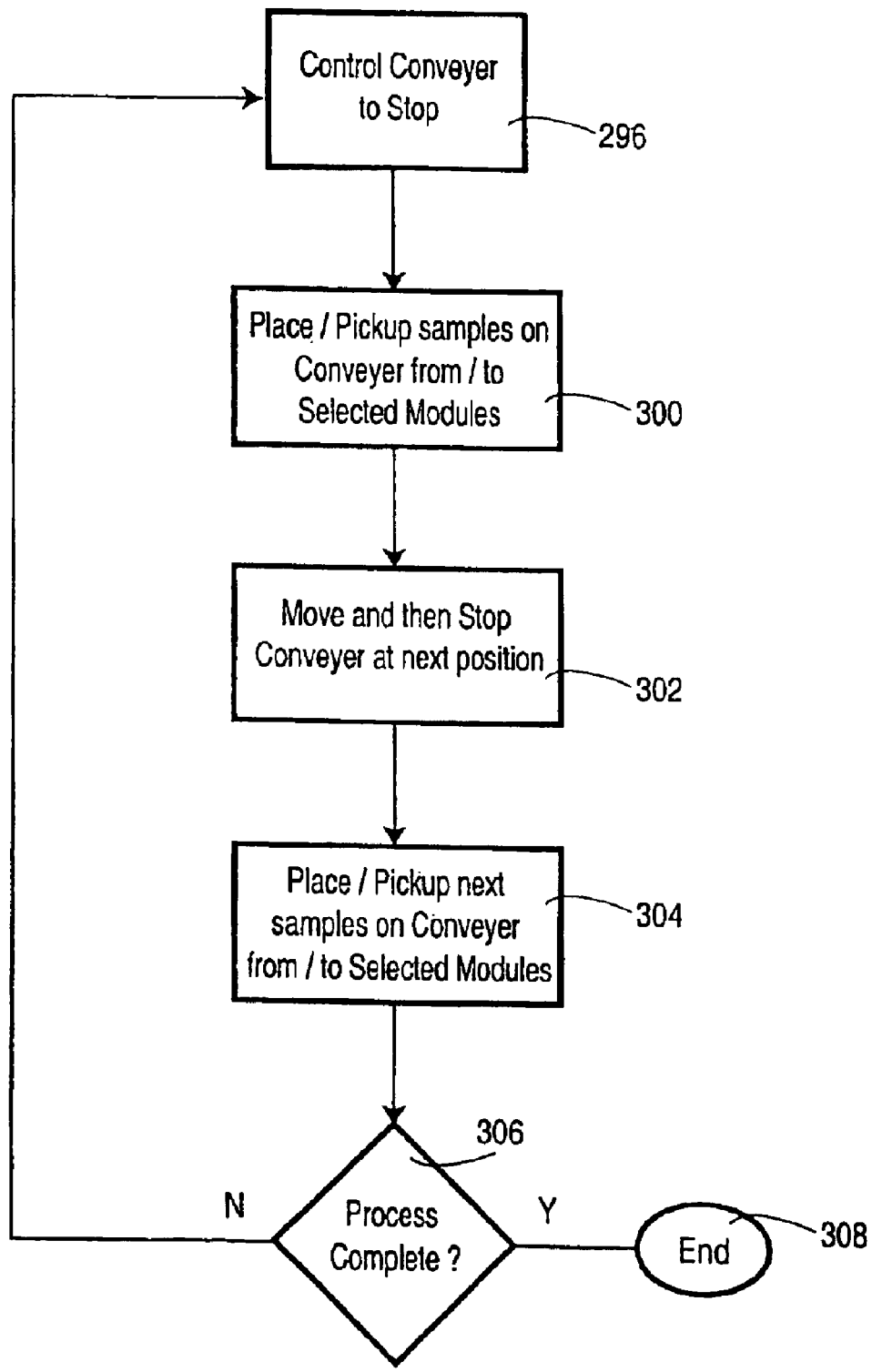
FIG. 20 is a method of operating the system of FIG. 1.

Referring to FIGS. 2 and 20, in operation of the robotic system 10, the motion between the instruments 14 can be done in three separate phases once the conveyer 19 is stopped 290, namely:

(i) Place 300 the sample 12 on the conveyer 19 by the local mover 26, wherein the sample 12 is picked out of the instrument 14 and placed on to the conveyer 19;

(ii) Convey 302 the sample 12 to the next adjacent module 16, wherein the conveyer 19 moves one or more samples 12 from one set of modules 16 to another set of modules 16 for further pick up and processing; and (iii) Place 304 sample 12 in the next instrument 14, wherein the sample 12 is picked off the conveyer 19 and placed into the local instrument 14 by the local mover 26.

Further, it is recognised the coordination between local mover 26 movement and the conveyer 19 movement can be such that, displacement of the sample 12 between the instrument 14 and the conveyer 19 by the mover 26 can be accomplished while the conveyer 19 is in motion. The mover 26 should be clear of the nest 32 on the conveyer 19 before motion of the conveyer 19 can either start or stop. therefore, the conveyer 19 is free to move once the movers 26 are clear of the conveyer 19 with associated samples 12.

The operation of the system 10 can also include decisions such as is the present processing of sample 12 set complete 306, and if so then end 308 the processing. Otherwise, the process can repeat at step 290. For multiple instruments 14, it is recognised that phases (i) and (iii) can be performed simultaneously. It is further recognised that the conveyer 19 does not move unless there is at least one sample 12 on it that has been scheduled for further processing by subsequent instruments 14, and that the conveyer 19 can be moved bi-directionally to facilitate transport of the samples 12 where needed It is further recognised that multiple samples 12 can be placed on the conveyer 19 and transported simultaneously to their next respective instrument 14.

Figure 21:
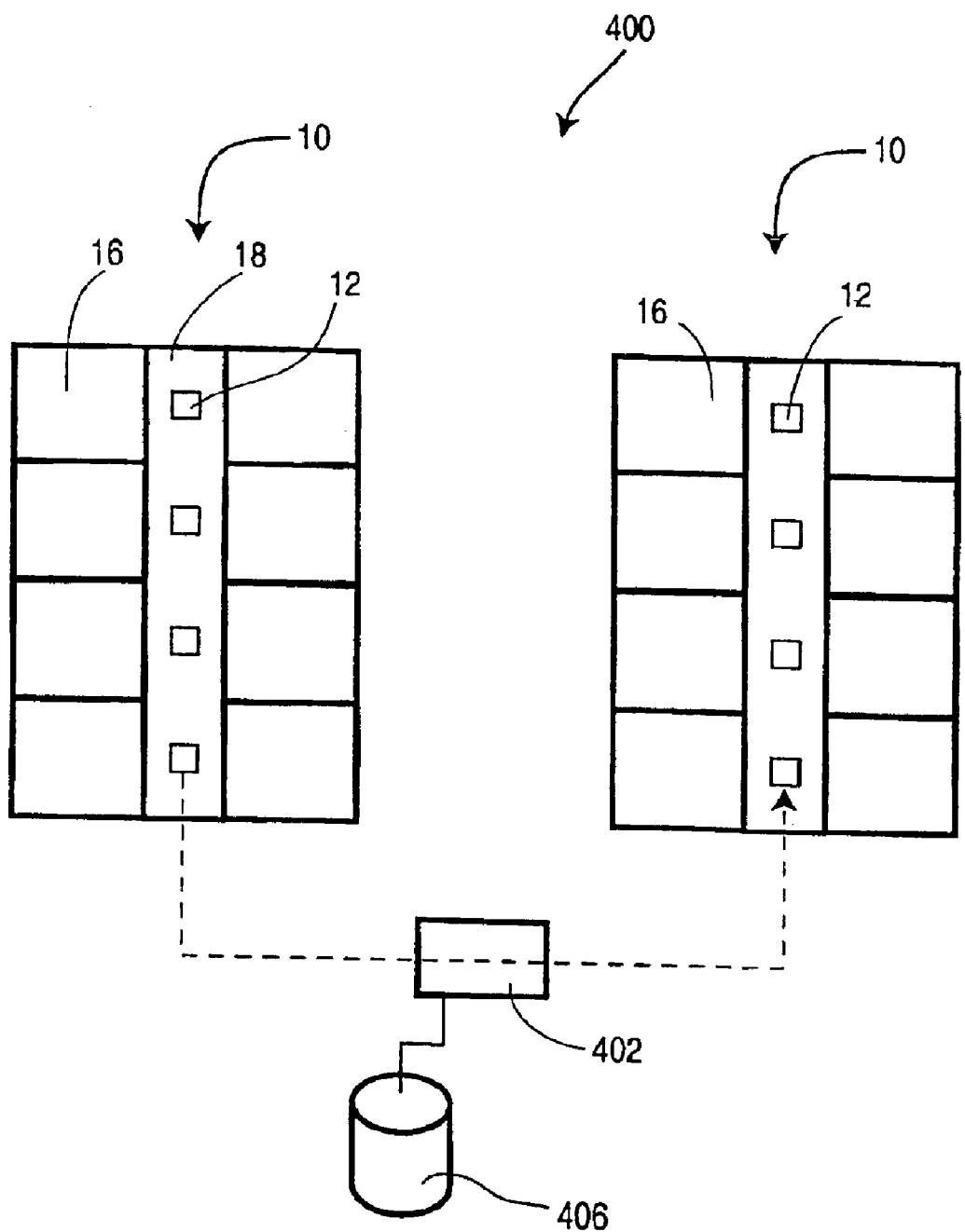
FIG. 21 is a further embodiment of the system of FIG. 1.

Referring to FIG. 21, a further embodiment of the system 10 can include multiple systems 10 operated in a coordinated manner, such that it creates a higher level processing system 400. For example, the systems 10 can be joined together with software and sample 12 transfers 402, but not physically coupled together. One embodiment is that the transfer mechanism 402 of samples 12 between the systems 10 can be with people, whereby the control architecture shown in FIG. 19 can direct people to shuttle the samples 12 between the systems 10 in a planned manner. This "man-in-the-loop" concept can use the mover control hierarchy 90 to actually command or otherwise prompt the people to move the samples 12 at the appropriate time between the systems 10. It is recognised that the host computer 104 (see FIG. 12) and/or the central control system 110 could coordinate the operation of the transfer mechanism 402. For example, an instrument server (not shown) could give instructions to the people, thereby providing the transfer mechanism 402.

Referring again to FIG. 21, the multiple systems 10 could be controlled via a higher level database 406, such as but not limited to a LIMS (lab information management system) as is known in the art. The database 406 could be operated by the host computer 104 and/or the central control system 110.

Further, is also envisioned that automatic, mobile or stationary moving devices could also serve as the transfer mechanism 402 to couple the multiple systems 10 together. For example, robots (not shown) could move the samples 12 between the systems 10, either such as but not limited to a mobile robot, or fixed robot arms.

Other unique features of the robotic system 10 can include: modules 16 being offered in different sizes to increase the number of possible configurations and maximize the system 10 flexibility; the ability to break the frame 150 down into pieces that can be packed flat on a skid; and cladding 172 for the ends of the frames 150. According to another feature, multiple discrete systems 10 can be used to create a higher-level system. This feature allows the communication and interaction of a group of related process steps, such as in situations where the automated process may be a sequence of steps in a complex method, while individual steps of such a method are executed on discrete systems. The system 10 can be applied to applications such as but not limited to Drug Discovery, Genomics and Proteomics, combi-chem, ADME/Tox, and lab processing.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. An automated robotic system having a modular architecture, the system comprising:
    a) a backbone having a plurality of backbone connectors;
    b) a module having a module connector for releasably coupling with a respective one of the backbone connectors;
    c) a bi-directional motion device connected to the backbone, the motion device for presenting an object adjacent to the module when the module is coupled to the backbone;
    d) a connection interface formable by coupling the backbone and module connectors, the connection interface for providing an operational coupling between the backbone and the module when adjacent thereto;
    wherein the connection interface provides a repeatable connection and disconnection capability between the backbone and the module for ready reconfiguration of the modular architecture.

2. The system of claim 1, wherein the connection interface when formed provides an operational interface between the backbone and the module, the operational interface selected from the group comprising; a mechanical alignment device, an electrical connection, a pneumatic connection, and a supply resource connection.

3. The system of claim 2, wherein the backbone connector is a first docking connector and the module connector is a second docking connector.

4. The system of claim 2, wherein the backbone connector is a set of cables and the module connector is a receptor adapted to connect with the cables.

5. The system of claim 2, wherein the module connector is a set of cables and the backbone connector is a receptor adapted to connect with the cables.

6. The system of claim 1 further comprising a plurality of the modules having respective module connectors, the plurality of modules coupled along the backbone.

7. The system of claim 6, wherein the motion device is a central linear object transport, the transport adapted to be used in conjunction with a plurality of local movers for transferring the transported objects from the transport to the modules.

8. The system of claim 7 further comprising a process instrument mounted on each of the modules.

9. The system of claim 8, wherein the local movers are mounted on the modules as a plurality of respective dedicated movers for each of the instruments, the dedicated movers for transferring the transported objects from the transport to their respective instrument.

10. The system of claim 8, wherein the local movers are mounted on the transport as central movers, the central movers for transferring transported objects between process instruments.

11. The system of claim 8 further comprising a plurality of movers mounted on the modules, the modules mounted along the length of the central transport in a fixed pitch arrangement, the fixed pitch arrangement for inhibiting interference between adjacent movers when transferring a respective one of the objects by each of the movers between the central transport and the respective instrument.

12. The system of claim 8 further comprising a plurality of movers mounted on the central transport, the movers mounted along the length of the central transport in a fixed pitch arrangement, the fixed pitch arrangement for inhibiting interference between adjacent movers when transferring a respective one of the objects by each of the movers between the central transport and the respective instrument.

13. The system of claim 6, wherein the arrangement of the modules provides a one-sided modular architecture.

14. The system of claim 6, wherein the arrangement of the modules provides a two-sided modular architecture with opposing modules on either side of the backbone.

15. The system of claim 6, wherein the motion device is an articulated robot.

16. The system of claim 6, wherein the motion device is a robot mounted on a linear track.

17. The system of claim 1 further comprising a rack mounting connected to at least one end of the backbone, the rack mounting for coupling electronic equipment to the backbone.

18. The system of claim 1, wherein the motion device is adapted to transport lab containers.

19. The system of claim 18, wherein the processing of samples in the lab containers is performed directly on the motion device.

20. The system of claim 18, wherein the processing of the samples is selected from the group comprising; delidding, barcode reading, and dispensing liquids.

21. The system of claim 20 further comprising a plurality of the modules having respective module connectors, the plurality of modules coupled along the backbone to respective backbone connectors.

22. The system of claim 21 further comprising a process instrument mounted on each of the modules.

23. The system of claim 22 further comprising individual local stacking units beside each of the instruments, the stacking units to provide destacking and restacking of the containers between the respective instrument and the stacking device transported by the motion device.

24. The system of claim 23, wherein each of the stacking units contains an empty, stationary stack so that the containers, once processed by the respective instrument, can be stacked into the empty stack, and then subsequently re-stacked into the original stacking device so that the order of the containers is preserved.

25. The system of claim 18 further comprising a stacking device for containing a plurality of the containers in a selected order.

26. The system of claim 25 further comprising a gripper attached to a mover for maintaining a grasp of the stacking device.

27. The system of claim 1 further comprising adjustable shims connected to a table surface of the module, the adjustable shims for bringing instruments to a common datum for loading.

28. The system of claim 1 for processing of the objects in applications selected from the group comprising; drug discovery, genomics, proteomics, combi-chem, ADME/Tox, and lab processing.

29. The system of claim 1, wherein the module further comprises a table with a support structure.

30. The system of claim 29, wherein the support structure is a self-contained structure capable of being used as a stand-alone or interconnected modular unit.

31. The system of claim 29 further comprising a table top of the table that can be lowered to a variety of selected heights.

32. The system of claim 29, wherein the module has a modular electrical power supply connection.

33. The system of claim 32, wherein the module further has a self-contained processing power and intelligence.

34. The system of claim 29, wherein the module has a bottom shelf that can be removed to accommodate storage under the table.

35. The system of claim 29, wherein the support structure can be disassembled and flat-packed.

36. The system of claim 29, wherein the module further comprises wheels and feet to allow both transport and levelling of the table on a supporting surface.

37. The system of claim 29, wherein the connection interface provides a hot-pluggability feature, such that an instrument associated with the module can be connected and disconnected while the system is running.

38. The system of claim 1, wherein the connection interface is a universal interface.

39. The system of claim 1, wherein the backbone is modular, such that the backbone further comprises a plurality of components, each of the components having a motion device connection interface for operationally coupling each of the components to form the backbone.

40. The system of claim 1 further comprising a plurality of controllers monitored by a host computer, the controllers for monitoring the operation of a series of local movers and the motion device.

41. The system of claim 40, wherein the controllers and the host computer form a central mover network, the central mover network for coordinating the simultaneous operation of the local movers and the central motion device.

42. The system of claim 41, wherein the controllers include a master controller and a plurality of slave controllers.

43. The system of claim 42, wherein each of the slave controllers have safety circuitry for emergency stop control.

44. The system of claim 40, wherein each of the controllers communicates on Ethernet protocol.

45. The system of claim 40, wherein each controller is adapted to control a predefined number of local movers.

46. A method of processing objects using a bilateral architecture, the method comprising the steps of:
  a) arranging a plurality of instruments around a bi-directional conveyance device, the instruments spaced at fixed pitch intervals along the conveyance device;
  b) assigning dedicated movers to each of the instruments, the dedicated movers for loading and unloading of the objects to and from the instruments and the conveyance device; and
  c) controlling the operation of the conveyance device to have an interrupted motion, the interrupted motion for coordinating the loading and unloading of the objects;
wherein the dedicated movers are positioned such that adjacent movers operate independently of one another.

47. The method of claim 46, wherein the movement of the objects between the instruments further comprises the steps of:
  a) transferring one of the objects from a selected one of the instruments to the conveyance device;
  b) conveying the transferred objects by the conveyance device to a subsequent one of the instruments;
  c) stopping the transport of the conveyance device; and
  d) transferring another of the objects from the conveyance to the subsequent instrument.

48. The method of claim 47, wherein the conveyance device does not move unless there is at least one object on the device.

49. The method of claim 48, wherein for multiple instruments and objects, steps (a) and (d) are performed simultaneously.

50. The method of claim 49, wherein for multiple objects are in motion at the same time on the conveyance device.

51. The method of claim 47, wherein the displacement of the object between the conveyance device and the instrument by a dedicated mover is done simultaneously with movement of the conveyance device, the movement of the conveyance device being interrupted when the object is exchanged between the mover and the conveyance device.

* * * * *